United States Patent [19]
Franco et al.

[11] Patent Number: 6,040,436
[45] Date of Patent: *Mar. 21, 2000

[54] NUCLEIC ACID ENCODING HUMAN NEURONAL CALCIUM CHANNEL SUBUNITS

[75] Inventors: Rodrigo Franco, Basking Ridge; Ai Ru Sun Chen, Piscataway; David Joseph Shuey, Plainsboro, all of N.J.

[73] Assignee: American Home Products Corporation, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/713,118

[22] Filed: Sep. 16, 1996

[51] Int. Cl.$^7$ ...................................................... C07H 21/02
[52] U.S. Cl. ........................ 536/23.1; 530/350; 536/23.5; 435/252.3; 435/320.1
[58] Field of Search .................................. 536/23.1, 23.5; 530/350; 435/252.3, 320.1

[56] References Cited

FOREIGN PATENT DOCUMENTS

| 0 507 170 A2 | 3/1992 | European Pat. Off. . |
| WO 93/04083 | 3/1993 | WIPO . |
| WO 95/04822 | 2/1995 | WIPO . |

OTHER PUBLICATIONS

Collin, T., et al., "Cloning, chromosomal location and functional expression of the human voltage–dependent calcium–channel β3 subunit", *Eur. J. Biochem.,* 220:257–262 (1994).

Williams, M.E., et al., Structure and Functional Expression of $\alpha_1$, $\alpha$, and βSubunits of a Novel Human Neuronal Calcium Channel Subtype, *Neuron,* 8:71–84 (1992).

Williams, M.E., et al., "Structure and Functional Expression of an ω–Conotoxin–Sensitive Human N–Type Calcium Channel", *Science,* 257:389–395 (1992).

Abstract, Society for Neuroscience, Meeting, Nov. 1994, Miami, Florida: *Soc. for Neuroscience Abstracts,* 20:34.10 (1994).

*Primary Examiner*—Bradley Sisson
*Assistant Examiner*—Janell E. Taylor
*Attorney, Agent, or Firm*—Hamilton, Brook, Smith & Reynolds, P.C.

[57] ABSTRACT

Nucleic acids encoding each of three subunits, α1B, α2δ, and β3, of a calcium channel, are disclosed. Also disclosed are vectors containing the nucleic acids encoding the subunits; host cells containing the nucleic acids encoding the subunits; methods of isolating nucleic acids encoding related calcium channel subunits; the subunit proteins; fusion proteins comprising the subunit proteins; antibodies to the subunit proteins; assays to identify agents that modulate calcium channel activity, and agents identified thereby; methods of treating certain central nervous system disorders by altering calcium channel activity; and methods of diagnosing diseases associated with particular calcium channels, such as Lambert-Eaton syndrome.

12 Claims, 1 Drawing Sheet

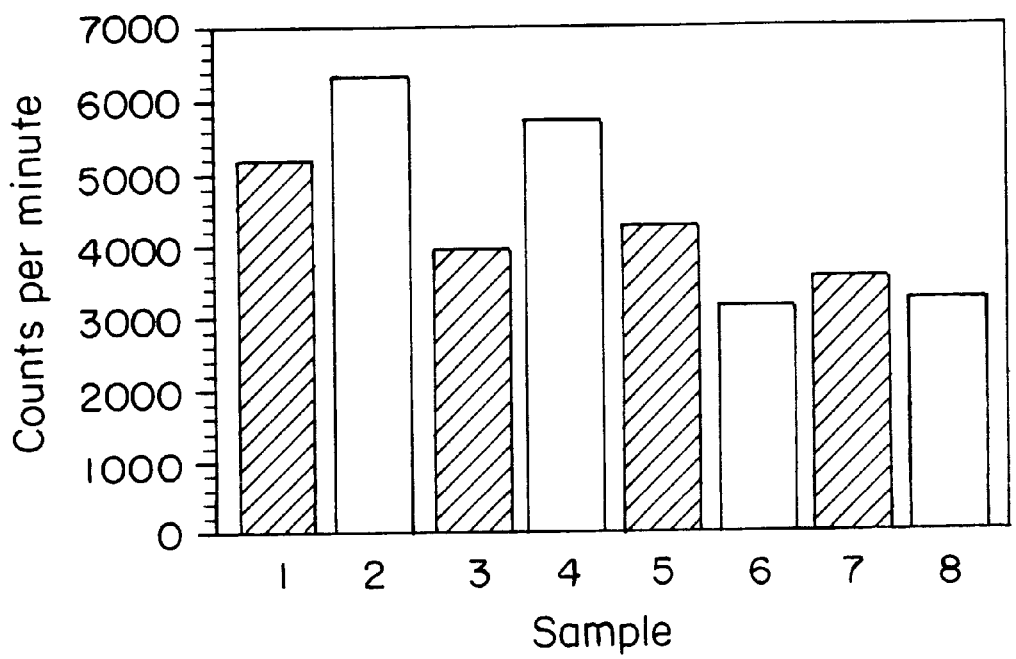

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 7266 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 92..7102

(xi) SEQUENCE DESCRIPTION: SEQ ID NO:1:

```
TCCGTGGCTG CTCCGCTCTG AGCGCCTGGC GCGCCCCGCG CCCTCCCTGC CGGGGCCGCT         60

GGGCCGGGGA TGCACGCGGG GCCCGGGAGC C ATG GTC CGC TTC GGG GAC GAG          112
                                 Met Val Arg Phe Gly Asp Glu
                                  1               5

CTG GGC GGC CGC TAT GGA GGC CCC GGC AGC GGA GAG CGG GCC CGG GGC         160
Leu Gly Gly Arg Tyr Gly Gly Pro Gly Ser Gly Glu Arg Ala Arg Gly
         10                  15                  20

GGC GGG GCC GGC GGG GCG GGG GGC CCG GGT CCC GGG GGG CTG CAG CCC         208
Gly Gly Ala Gly Gly Ala Gly Gly Pro Gly Pro Gly Gly Leu Gln Pro
     25                  30                  35

GGC CAG CGG GTC CTC TAC AAG CAA TCG ATC GCG CAG CGC GCG CGG ACC         256
Gly Gln Arg Val Leu Tyr Lys Gln Ser Ile Ala Gln Arg Ala Arg Thr
 40                  45                  50                  55

ATG GCG CTG TAC AAC CCC ATC CCG GTC AAG CAG AAC TGC TTC ACC GTC         304
Met Ala Leu Tyr Asn Pro Ile Pro Val Lys Gln Asn Cys Phe Thr Val
                 60                  65                  70

AAC CGC TCG CTC TTC GTC TTC AGC GAG GAC AAC GTC GTC CGC AAA TAC         352
```

-continued

```
                Asn Arg Ser Leu Phe Val Phe Ser Glu Asp Asn Val Val Arg Lys Tyr
                             75                  80                  85

GCG AAG CGC ATC ACC GAG TGG CCT CCA TTC GAG TAT ATG ATC CTG GCC                400
Ala Lys Arg Ile Thr Glu Trp Pro Pro Phe Glu Tyr Met Ile Leu Ala
         90                  95                 100

ACC ATC ATC GCC AAC TGC ATC GTG CTG GCC CTG GAG CAG CAC CTC CCT                448
Thr Ile Ile Ala Asn Cys Ile Val Leu Ala Leu Glu Gln His Leu Pro
105                 110                 115

GAT GGG GAC AAA ACG CCC ATG TCC GAG CGG CTG GAC GAC ACG GAG CCC                496
Asp Gly Asp Lys Thr Pro Met Ser Glu Arg Leu Asp Asp Thr Glu Pro
120                 125                 130                 135

TAT TTC ATC GGG ATC TTT TGC TTC GAG GCA GGG ATC AAA ATC ATC GCT                544
Tyr Phe Ile Gly Ile Phe Cys Phe Glu Ala Gly Ile Lys Ile Ile Ala
                140                 145                 150

CTG GGC TTT GTC TTC CAC AAG GGC TCT TAC CTG CGG AAC GGC TGG AAC                592
Leu Gly Phe Val Phe His Lys Gly Ser Tyr Leu Arg Asn Gly Trp Asn
                155                 160                 165

GTC ATG GAC TTC GTG GTC GTC CTC ACA GGG ATC CTT GCC ACG GCT GGA                640
Val Met Asp Phe Val Val Val Leu Thr Gly Ile Leu Ala Thr Ala Gly
                170                 175                 180

ACT GAC TTC GAC CTG CGA ACA CTG AGG GCT GTG CGT GTG CTG AGG CCC                688
Thr Asp Phe Asp Leu Arg Thr Leu Arg Ala Val Arg Val Leu Arg Pro
                185                 190                 195

CTG AAG CTG GTG TCT GGG ATT CCA AGT TTG CAG GTG GTG CTC AAG TCC                736
Leu Lys Leu Val Ser Gly Ile Pro Ser Leu Gln Val Val Leu Lys Ser
200                 205                 210                 215

ATC ATG AAG GCC ATG GTT CCA CTC CTG CAG ATT GGG CTG CTT CTC TTC                784
Ile Met Lys Ala Met Val Pro Leu Leu Gln Ile Gly Leu Leu Leu Phe
                220                 225                 230

TTT GCC ATC CTC ATG TTT GCC ATC ATT GGC CTG GAG TTC TAC ATG GGC                832
Phe Ala Ile Leu Met Phe Ala Ile Ile Gly Leu Glu Phe Tyr Met Gly
                235                 240                 245

AAG TTC CAC AAG GCC TGT TTC CCC AAC AGC ACA GAT GCG GAG CCC GTG                880
Lys Phe His Lys Ala Cys Phe Pro Asn Ser Thr Asp Ala Glu Pro Val
                250                 255                 260

GGT GAC TTC CCC TGT GGC AAG GAG GCC CCA GCC CGG CTG TGC GAG GGC                928
Gly Asp Phe Pro Cys Gly Lys Glu Ala Pro Ala Arg Leu Cys Glu Gly
                265                 270                 275

GAC ACT GAG TGC CGG GAG TAC TGG CCA GGA CCC AAC TTT GGC ATC ACC                976
Asp Thr Glu Cys Arg Glu Tyr Trp Pro Gly Pro Asn Phe Gly Ile Thr
280                 285                 290                 295

AAC TTT GAC AAT ATC CTG TTT GCC ATC TTG ACG GTG TTC CAG TGC ATC               1024
Asn Phe Asp Asn Ile Leu Phe Ala Ile Leu Thr Val Phe Gln Cys Ile
                300                 305                 310

ACC ATG GAG GGC TGG ACT GAC ATC CTC TAT AAT ACA AAC GAT GCG GCC               1072
Thr Met Glu Gly Trp Thr Asp Ile Leu Tyr Asn Thr Asn Asp Ala Ala
                315                 320                 325

GGC AAC ACC TGG AAC TGG CTC TAC TTC ATC CCT CTC ATC ATC ATC GGC               1120
Gly Asn Thr Trp Asn Trp Leu Tyr Phe Ile Pro Leu Ile Ile Ile Gly
                330                 335                 340

TCC TTC TTC ATG CTC AAC CTG GTG CTG GGC GTG CTC TCG GGG GAG TTT               1168
Ser Phe Phe Met Leu Asn Leu Val Leu Gly Val Leu Ser Gly Glu Phe
                345                 350                 355

GCC AAG GAG CGA GAG AGG GTG GAG AAC CGC CGC GCC TTC CTG AAG CTG               1216
Ala Lys Glu Arg Glu Arg Val Glu Asn Arg Arg Ala Phe Leu Lys Leu
360                 365                 370                 375

CGC CGG CAG CAG CAG ATC GAG CGA GAG CTC AAC GGG TAC CTG GAG TGG               1264
Arg Arg Gln Gln Gln Ile Glu Arg Glu Leu Asn Gly Tyr Leu Glu Trp
                380                 385                 390
```

-continued

| | |
|---|---|
| ATC TTC AAG GCG GAG GAA GTC ATG CTG GCC GAG GAG GAC AGG AAT GCA<br>Ile Phe Lys Ala Glu Glu Val Met Leu Ala Glu Glu Asp Arg Asn Ala<br>     395          400         405 | 1312 |
| GAG GAG AAG TCC CCT TTG GAC GTG CTG AAG AGA GCG GCC ACC AAG AAG<br>Glu Glu Lys Ser Pro Leu Asp Val Leu Lys Arg Ala Ala Thr Lys Lys<br>     410          415         420 | 1360 |
| AGC AGA AAT GAC CTG ATC CAC GCA GAG GAG GGA GAG GAC CGG TTT GCA<br>Ser Arg Asn Asp Leu Ile His Ala Glu Glu Gly Glu Asp Arg Phe Ala<br>        425          430         435 | 1408 |
| GAT CTC TGT GCT GTT GGA TCC CCC TTC GCC CGC GCC AGC CTC AAG AGC<br>Asp Leu Cys Ala Val Gly Ser Pro Phe Ala Arg Ala Ser Leu Lys Ser<br>440          445          450        455 | 1456 |
| GGG AAG ACA GAG AGC TCG TCA TAC TTC CGG AGG AAG GAG AAG ATG TTC<br>Gly Lys Thr Glu Ser Ser Ser Tyr Phe Arg Arg Lys Glu Lys Met Phe<br>          460          465        470 | 1504 |
| CGG TTT TTT ATC CGG CGC ATG GTG AAG GCT CAG AGC TTC TAC TGG GTG<br>Arg Phe Phe Ile Arg Arg Met Val Lys Ala Gln Ser Phe Tyr Trp Val<br>        475          480         485 | 1552 |
| GTG CTG TGC GTG GTG GCC CTG AAC ACA CTG TGT GTG GCC ATG GTG CAT<br>Val Leu Cys Val Val Ala Leu Asn Thr Leu Cys Val Ala Met Val His<br>     490          495         500 | 1600 |
| TAC AAC CAG CCG CGG CGG CTT ACC ACG ACC CTG TAT TTT GCA GAG TTT<br>Tyr Asn Gln Pro Arg Arg Leu Thr Thr Thr Leu Tyr Phe Ala Glu Phe<br>505           510         515 | 1648 |
| GTT TTC CTG GGT CTC TTC CTC ACA GAG ATG TCC CTG AAG ATG TAT GGC<br>Val Phe Leu Gly Leu Phe Leu Thr Glu Met Ser Leu Lys Met Tyr Gly<br>520          525          530        535 | 1696 |
| CTG GGG CCC AGA AGC TAC TTC CGG TCC TCC TTC AAC TGC TTC GAC TTT<br>Leu Gly Pro Arg Ser Tyr Phe Arg Ser Ser Phe Asn Cys Phe Asp Phe<br>          540          545        550 | 1744 |
| GGG GTC ATC GTG GGG AGC GTC TTT GAA GTG GTC TGG GCG GCC ATC AAG<br>Gly Val Ile Val Gly Ser Val Phe Glu Val Val Trp Ala Ala Ile Lys<br>        555          560         565 | 1792 |
| CCG GGA AGC TCC TTT GGG ATC AGT GTG CTG CGG GCC CTC CGC CTG CTG<br>Pro Gly Ser Ser Phe Gly Ile Ser Val Leu Arg Ala Leu Arg Leu Leu<br>     570          575         580 | 1840 |
| AGG ATC TTC AAA GTC ACG AAG TAC TGG AGC TCC CTG CGG AAC CTG GTG<br>Arg Ile Phe Lys Val Thr Lys Tyr Trp Ser Ser Leu Arg Asn Leu Val<br>585          590          595 | 1888 |
| GTG TCC CTG CTG AAC TCC ATG AAG TCC ATC ATC AGC CTG CTC TTC TTG<br>Val Ser Leu Leu Asn Ser Met Lys Ser Ile Ile Ser Leu Leu Phe Leu<br>600          605         610        615 | 1936 |
| CTC TTC CTG TTC ATT GTG GTC TTC GCC CTG CTG GGG ATG CAG CTG TTT<br>Leu Phe Leu Phe Ile Val Val Phe Ala Leu Leu Gly Met Gln Leu Phe<br>        620          625        630 | 1984 |
| GGG GGA CAG TTC AAC TTC CAG GAT GAG ACT CCC ACA ACC AAC TTC GAC<br>Gly Gly Gln Phe Asn Phe Gln Asp Glu Thr Pro Thr Thr Asn Phe Asp<br>     635          640         645 | 2032 |
| ACC TTC CCT GCC GCC ATC CTC ACT GTC TTC CAG ATC CTG ACG GGA GAG<br>Thr Phe Pro Ala Ala Ile Leu Thr Val Phe Gln Ile Leu Thr Gly Glu<br>650          655         660 | 2080 |
| GAC TGG AAT GCA GTG ATG TAT CAC GGG ATC GAA TCG CAA GGC GGC GTC<br>Asp Trp Asn Ala Val Met Tyr His Gly Ile Glu Ser Gln Gly Gly Val<br>     665          670         675 | 2128 |
| AGC AAA GGC ATG TTC TCG TCC TTT TAC TTC ATT GTC CTG ACA CTG TTC<br>Ser Lys Gly Met Phe Ser Ser Phe Tyr Phe Ile Val Leu Thr Leu Phe<br>680          685         690        695 | 2176 |
| GGA AAC TAC ACT CTG CTG AAT GTC TTT CTG GCC ATC GCT GTG GAC AAC<br>Gly Asn Tyr Thr Leu Leu Asn Val Phe Leu Ala Ile Ala Val Asp Asn<br>          700          705        710 | 2224 |

```
CTG GCC AAC GCC CAA GAG CTG ACC AAG GAT GAA GAG GAG ATG GAA GAA        2272
Leu Ala Asn Ala Gln Glu Leu Thr Lys Asp Glu Glu Glu Met Glu Glu
            715                 720                 725

GCA GCC AAT CAG AAG CTT GCT CTG CAA AAG GCC AAA GAA GTG GCT GAA        2320
Ala Ala Asn Gln Lys Leu Ala Leu Gln Lys Ala Lys Glu Val Ala Glu
            730                 735                 740

GTC AGC CCC ATG TCT GCC GCG AAC ATC TCC ATC GCC GCC AGG CAG CAG        2368
Val Ser Pro Met Ser Ala Ala Asn Ile Ser Ile Ala Ala Arg Gln Gln
745                 750                 755

AAC TCG GCC AAG GCG CGC TCG GTG TGG GAG CAG CGG GCC AGC CAG CTA        2416
Asn Ser Ala Lys Ala Arg Ser Val Trp Glu Gln Arg Ala Ser Gln Leu
760                 765                 770                 775

CGG CTG CAG AAC CTG CGG GCC AGC TGC GAG GCG CTG TAC AGC GAG ATG        2464
Arg Leu Gln Asn Leu Arg Ala Ser Cys Glu Ala Leu Tyr Ser Glu Met
                780                 785                 790

GAC CCC GAG GAG CGG CTG CGC TTC GCC ACT ACG CGC CAC CGG CGG CCC        2512
Asp Pro Glu Glu Arg Leu Arg Phe Ala Thr Thr Arg His Arg Arg Pro
                795                 800                 805

GAC ATG AAG ACG CAC CTG GAC CGG CCG CTG GTG GTG GAG CTG GGC CGC        2560
Asp Met Lys Thr His Leu Asp Arg Pro Leu Val Val Glu Leu Gly Arg
            810                 815                 820

GAC GGC GCG CGG GGG CCC GTG GGA GGC AAA GCC CGA CCT GAG GCT GCG        2608
Asp Gly Ala Arg Gly Pro Val Gly Gly Lys Ala Arg Pro Glu Ala Ala
825                 830                 835

GAG GCC CCC GAG GGC GTC GAC CCT CCG CGC AGG CAC CAC CGG CAC CGC        2656
Glu Ala Pro Glu Gly Val Asp Pro Pro Arg Arg His His Arg His Arg
840                 845                 850                 855

GAC AAG GAC AAG ACC CCC GCG GCG GGG GAC CAG GAC CGA GCA GAG GCC        2704
Asp Lys Asp Lys Thr Pro Ala Ala Gly Asp Gln Asp Arg Ala Glu Ala
                860                 865                 870

CCG AAG GCG GAG AGC GGG GAG CCC GGT GCC CGG GAG GAG CGG CCG CGG        2752
Pro Lys Ala Glu Ser Gly Glu Pro Gly Ala Arg Glu Glu Arg Pro Arg
                875                 880                 885

CCG CAC CGC AGC CAC AGC AAG GAG GCC GCG GGG CCC CCG GAG GCG CGG        2800
Pro His Arg Ser His Ser Lys Glu Ala Ala Gly Pro Pro Glu Ala Arg
            890                 895                 900

AGC GAG CGC GGC CGA GGC CCA GGC CCC GAG GGC GGC CGG CGG CAC CAC        2848
Ser Glu Arg Gly Arg Gly Pro Gly Pro Glu Gly Gly Arg Arg His His
905                 910                 915

CGG CGC GGC TCC CCG GAG GAG GCG GCC GAG CGG GAG CCC CGA CGC CAC        2896
Arg Arg Gly Ser Pro Glu Glu Ala Ala Glu Arg Glu Pro Arg Arg His
920                 925                 930                 935

CGC GCG CAC CGG CAC CAG GAT CCG AGC AAG GAG TGC GCC GGC GCC AAG        2944
Arg Ala His Arg His Gln Asp Pro Ser Lys Glu Cys Ala Gly Ala Lys
                940                 945                 950

GGC GAG CGG CGC GCG CGG CAC CGC GGC GGC CCC CGA GCG GGG CCC CGG        2992
Gly Glu Arg Arg Ala Arg His Arg Gly Gly Pro Arg Ala Gly Pro Arg
            955                 960                 965

GAG GCG GAG AGC GGG GAG GAG CCG GCG CGG CGG CAC CGG GCC CGG CAC        3040
Glu Ala Glu Ser Gly Glu Glu Pro Ala Arg Arg His Arg Ala Arg His
            970                 975                 980

AAG GCG CAG CCT GCT CAC GAG GCT GTG GAG AAG GAG ACC ACG GAG AAG        3088
Lys Ala Gln Pro Ala His Glu Ala Val Glu Lys Glu Thr Thr Glu Lys
985                 990                 995

GAG GCC ACG GAG AAG GAG GCT GAG ATA GTG GAA GCC GAC AAG GAA AAG        3136
Glu Ala Thr Glu Lys Glu Ala Glu Ile Val Glu Ala Asp Lys Glu Lys
1000                1005                1010                1015

GAG CTC CGG AAC CAC CAG CCC CGG GAG CCA CAC TGT GAC CTG GAG ACC        3184
Glu Leu Arg Asn His Gln Pro Arg Glu Pro His Cys Asp Leu Glu Thr
```

```
                          1020                  1025                  1030
AGT GGG ACT GTG ACT GTG GGT CCC ATG CAC ACA CTG CCC AGC ACC TGT        3232
Ser Gly Thr Val Thr Val Gly Pro Met His Thr Leu Pro Ser Thr Cys
            1035                  1040                  1045

CTC CAG AAG GTG GAG GAA CAG CCA GAG GAT GCA GAC AAT CAG CGG AAC        3280
Leu Gln Lys Val Glu Glu Gln Pro Glu Asp Ala Asp Asn Gln Arg Asn
            1050                  1055                  1060

GTC ACT CGC ATG GGC AGT CAG CCC CCA GAC CCG AAC ACT ATT GTA CAT        3328
Val Thr Arg Met Gly Ser Gln Pro Pro Asp Pro Asn Thr Ile Val His
            1065                  1070                  1075

ATC CCA GTG ATG CTG ACG GGC CCT CTT GGG GAA GCC ACG GTC GTT CCC        3376
Ile Pro Val Met Leu Thr Gly Pro Leu Gly Glu Ala Thr Val Val Pro
1080                  1085                  1090                  1095

AGT GGT AAC GTG GAC CTG GAA AGC CAA GCA GAG GGG AAG AAG GAG GTG        3424
Ser Gly Asn Val Asp Leu Glu Ser Gln Ala Glu Gly Lys Lys Glu Val
            1100                  1105                  1110

GAA GCG GAT GAC GTG ATG AGG AGC GGC CCC CGG CCT ATC GTC CCA TAC        3472
Glu Ala Asp Asp Val Met Arg Ser Gly Pro Arg Pro Ile Val Pro Tyr
            1115                  1120                  1125

AGC TCC ATG TTC TGT TTA AGC CCC ACC AAC CTG CTC CGC CGC TTC TGC        3520
Ser Ser Met Phe Cys Leu Ser Pro Thr Asn Leu Leu Arg Arg Phe Cys
            1130                  1135                  1140

CAC TAC ATC GTG ACC ATG AGG TAC TTC GAG GTG GTC ATT CTC GTG GTC        3568
His Tyr Ile Val Thr Met Arg Tyr Phe Glu Val Val Ile Leu Val Val
            1145                  1150                  1155

ATC GCC TTG AGC AGC ATC GCC CTG GCT GCT GAG GAC CCA GTG CGC ACA        3616
Ile Ala Leu Ser Ser Ile Ala Leu Ala Ala Glu Asp Pro Val Arg Thr
1160                  1165                  1170                  1175

GAC TCG CCC AGG AAC AAC GCT CTG AAA TAC CTG GAT TAC ATT TTC ACT        3664
Asp Ser Pro Arg Asn Asn Ala Leu Lys Tyr Leu Asp Tyr Ile Phe Thr
            1180                  1185                  1190

GGT GTC TTT ACC TTT GAG ATG GTG ATA AAG ATG ATC GAC TTG GGA CTG        3712
Gly Val Phe Thr Phe Glu Met Val Ile Lys Met Ile Asp Leu Gly Leu
            1195                  1200                  1205

CTG CTT CAC CCT GGA GCC TAT TTC CGG GAC TTG TGG AAC ATT CTG GAC        3760
Leu Leu His Pro Gly Ala Tyr Phe Arg Asp Leu Trp Asn Ile Leu Asp
            1210                  1215                  1220

TTC ATT GTG GTC AGT GGC GCC CTG GTG GCG TTT GCT TTC TCA GGA TCC        3808
Phe Ile Val Val Ser Gly Ala Leu Val Ala Phe Ala Phe Ser Gly Ser
            1225                  1230                  1235

AAA GGG AAA GAC ATC AAT ACC ATC AAG TCT CTG AGA GTC CTT CGT GTC        3856
Lys Gly Lys Asp Ile Asn Thr Ile Lys Ser Leu Arg Val Leu Arg Val
1240                  1245                  1250                  1255

CTG CGG CCC CTC AAG ACC ATC AAA CGG CTG CCC AAG CTC AAG GCT GTG        3904
Leu Arg Pro Leu Lys Thr Ile Lys Arg Leu Pro Lys Leu Lys Ala Val
            1260                  1265                  1270

TTT GAC TGT GTG GTG AAC TCC CTG AAG AAT GTC CTC AAC ATC TTG ATT        3952
Phe Asp Cys Val Val Asn Ser Leu Lys Asn Val Leu Asn Ile Leu Ile
            1275                  1280                  1285

GTC TAC ATG CTC TTC ATG TTC ATA TTT GCC GTC ATT GCG GTG CAG CTC        4000
Val Tyr Met Leu Phe Met Phe Ile Phe Ala Val Ile Ala Val Gln Leu
            1290                  1295                  1300

TTC AAA GGG AAG TTT TTC TAC TGC ACA GAT GAA TCC AAG GAG CTG GAG        4048
Phe Lys Gly Lys Phe Phe Tyr Cys Thr Asp Glu Ser Lys Glu Leu Glu
            1305                  1310                  1315

AGG GAC TGC AGG GGT CAG TAT TTG GAT TAT GAG AAG GAG GAA GTG GAA        4096
Arg Asp Cys Arg Gly Gln Tyr Leu Asp Tyr Glu Lys Glu Glu Val Glu
1320                  1325                  1330                  1335

GCT CAG CCC AGG CAG TGG AAG AAA TAC GAC TTT CAC TAC GAC AAT GTG        4144
```

```
Ala Gln Pro Arg Gln Trp Lys Lys Tyr Asp Phe His Tyr Asp Asn Val
            1340                1345                1350

CTC TGG GCT CTG CTG ACG CTG TTC ACA GTG TCC ACG GGA GAA GGC TGG      4192
Leu Trp Ala Leu Leu Thr Leu Phe Thr Val Ser Thr Gly Glu Gly Trp
        1355                1360                1365

CCC ATG GTG CTG AAA CAC TCC GTG GAT GCC ACC TAT GAG GAG CAG GGT      4240
Pro Met Val Leu Lys His Ser Val Asp Ala Thr Tyr Glu Glu Gln Gly
    1370                1375                1380

CCA AGC CCT GGG TAC CGC ATG GAG CTG TCC ATC TTC TAC GTG GTC TAC      4288
Pro Ser Pro Gly Tyr Arg Met Glu Leu Ser Ile Phe Tyr Val Val Tyr
1385                1390                1395

TTT GTG GTC TTT CCC TTC TTC TTC GTC AAC ATC TTT GTG GCT TTG ATC      4336
Phe Val Val Phe Pro Phe Phe Phe Val Asn Ile Phe Val Ala Leu Ile
1400                1405                1410                1415

ATC ATC ACC TTC CAG GAG CAG GGG GAC AAG GTG ATG TCT GAA TGC AGC      4384
Ile Ile Thr Phe Gln Glu Gln Gly Asp Lys Val Met Ser Glu Cys Ser
                1420                1425                1430

CTG GAG AAG AAC GAG AGG GCT TGC ATT GAC TTC GCC ATC AGC GCC AAA      4432
Leu Glu Lys Asn Glu Arg Ala Cys Ile Asp Phe Ala Ile Ser Ala Lys
            1435                1440                1445

CCC CTG ACA CGG TAC ATG CCC CAA AAC CGG CAG TCG TTC CAG TAT AAG      4480
Pro Leu Thr Arg Tyr Met Pro Gln Asn Arg Gln Ser Phe Gln Tyr Lys
        1450                1455                1460

ACG TGG ACA TTT GTG GTC TCC CCG CCC TTT GAA TAC TTC ATC ATG GCC      4528
Thr Trp Thr Phe Val Val Ser Pro Pro Phe Glu Tyr Phe Ile Met Ala
    1465                1470                1475

ATG ATA GCC CTC AAC ACT GTG GTG CTG ATG ATG AAG TTC TAT GAT GCA      4576
Met Ile Ala Leu Asn Thr Val Val Leu Met Met Lys Phe Tyr Asp Ala
1480                1485                1490                1495

CCC TAT GAG TAC GAG CTG ATG CTG AAA TGC CTG AAC ATC GTG TTC ACA      4624
Pro Tyr Glu Tyr Glu Leu Met Leu Lys Cys Leu Asn Ile Val Phe Thr
                1500                1505                1510

TCC ATG TTC TCC ATG GAA TGC GTG CTG AAG ATC ATC GCC TTT GGG GTG      4672
Ser Met Phe Ser Met Glu Cys Val Leu Lys Ile Ile Ala Phe Gly Val
            1515                1520                1525

CTG AAC TAT TTC AGA GAT GCC TGG AAT GTC TTT GAC TTT GTC ACT GTG      4720
Leu Asn Tyr Phe Arg Asp Ala Trp Asn Val Phe Asp Phe Val Thr Val
        1530                1535                1540

TTG GGA AGT ATT ACT GAT ATT TTA GTA ACA GAG ATT GCG AAC AAT TTC      4768
Leu Gly Ser Ile Thr Asp Ile Leu Val Thr Glu Ile Ala Asn Asn Phe
    1545                1550                1555

ATC AAC CTC AGC TTC CTC CGC CTC TTT CGA GCT GCG CGG CTG ATC AAG      4816
Ile Asn Leu Ser Phe Leu Arg Leu Phe Arg Ala Ala Arg Leu Ile Lys
1560                1565                1570                1575

CTG CTC CGC CAG GGC TAC ACC ATC CGC ATC CTG CTG TGG ACC TTT GTC      4864
Leu Leu Arg Gln Gly Tyr Thr Ile Arg Ile Leu Leu Trp Thr Phe Val
                1580                1585                1590

CAG TCC TTC AAG GCC CTG CCC TAC GTG TGT CTG CTC ATT GCC ATG CTG      4912
Gln Ser Phe Lys Ala Leu Pro Tyr Val Cys Leu Leu Ile Ala Met Leu
            1595                1600                1605

TTC TTC ATC TAC GCC ATC ATC GGC ATG CAG GTG TTT GGG AAT ATT GCC      4960
Phe Phe Ile Tyr Ala Ile Ile Gly Met Gln Val Phe Gly Asn Ile Ala
        1610                1615                1620

CTG GAT GAT GAC ACC AGC ATC AAC CGC CAC AAC AAC TTC CGG ACG TTT      5008
Leu Asp Asp Asp Thr Ser Ile Asn Arg His Asn Asn Phe Arg Thr Phe
    1625                1630                1635

TTG CAA GCC CTG ATG CTG CTG TTC AGG AGC GCC ACG GGG GAG GCC TGG      5056
Leu Gln Ala Leu Met Leu Leu Phe Arg Ser Ala Thr Gly Glu Ala Trp
1640                1645                1650                1655
```

-continued

```
CAC GAG ATC ATG CTG TCC TGC CTG AGC AAC CAG GCC TGT GAT GAG CAG         5104
His Glu Ile Met Leu Ser Cys Leu Ser Asn Gln Ala Cys Asp Glu Gln
             1660                1665                1670

GCC AAT GCC ACC GAG TGT GGA AGT GAC TTT GCC TAC TTC TAC TTC GTC         5152
Ala Asn Ala Thr Glu Cys Gly Ser Asp Phe Ala Tyr Phe Tyr Phe Val
             1675                1680                1685

TCC TTC ATC TTC CTG TGC TCC TTT CTG ATG TTG AAC CTC TTT GTG GCT         5200
Ser Phe Ile Phe Leu Cys Ser Phe Leu Met Leu Asn Leu Phe Val Ala
             1690                1695                1700

GTG ATC ATG GAC AAT TTT GAG TAC CTC ACG CGG GAC TCT TCC ATC CTA         5248
Val Ile Met Asp Asn Phe Glu Tyr Leu Thr Arg Asp Ser Ser Ile Leu
             1705                1710                1715

GGT CCT CAC CAC TTG GAT GAG TTC ATC CGG GTC TGG GCT GAA TAC GAC         5296
Gly Pro His His Leu Asp Glu Phe Ile Arg Val Trp Ala Glu Tyr Asp
1720                1725                1730                1735

CCG GCT GCG TGT GGG CGC ATC AGT TAC AAT GAC ATG TTT GAG ATG CTG         5344
Pro Ala Ala Cys Gly Arg Ile Ser Tyr Asn Asp Met Phe Glu Met Leu
             1740                1745                1750

AAA CAC ATG TCC CCG CCT CTG GGG CTG GGG AAG AAA TGC CCT GCT CGA         5392
Lys His Met Ser Pro Pro Leu Gly Leu Gly Lys Lys Cys Pro Ala Arg
             1755                1760                1765

GTT GCT TAC AAG CGC CTG GTT CGC ATG AAC ATG CCC ATC TCC AAC GAG         5440
Val Ala Tyr Lys Arg Leu Val Arg Met Asn Met Pro Ile Ser Asn Glu
             1770                1775                1780

GAC ATG ACT GTT CAC TTC ACG TCC ACG CTG ATG GCC CTC ATC CGG ACG         5488
Asp Met Thr Val His Phe Thr Ser Thr Leu Met Ala Leu Ile Arg Thr
             1785                1790                1795

GCA CTG GAG ATC AAG CTG GCC CCA GCT GGG ACA AAG CAG CAT CAG TGT         5536
Ala Leu Glu Ile Lys Leu Ala Pro Ala Gly Thr Lys Gln His Gln Cys
1800                1805                1810                1815

GAC GCG GAG TTG AGG AAG GAG ATT TCC GTT GTG TGG GCC AAT CTG CCC         5584
Asp Ala Glu Leu Arg Lys Glu Ile Ser Val Val Trp Ala Asn Leu Pro
             1820                1825                1830

CAG AAG ACT TTG GAC TTG CTG GTA CCA CCC CAT AAG CCT GAT GAG ATG         5632
Gln Lys Thr Leu Asp Leu Leu Val Pro Pro His Lys Pro Asp Glu Met
             1835                1840                1845

ACA GTG GGG AAG GTT TAT GCA GCT CTG ATG ATA TTT GAC TTC TAC AAG         5680
Thr Val Gly Lys Val Tyr Ala Ala Leu Met Ile Phe Asp Phe Tyr Lys
             1850                1855                1860

CAG AAC AAA ACC ACC AGA GAC CAG ATG CAG CAG GCT CCT GGA GGC CTC         5728
Gln Asn Lys Thr Thr Arg Asp Gln Met Gln Gln Ala Pro Gly Gly Leu
             1865                1870                1875

TCC CAG ATG GGT CCT GTG TCC CTG TTC CAC CCT CTG AAG GCC ACC CTG         5776
Ser Gln Met Gly Pro Val Ser Leu Phe His Pro Leu Lys Ala Thr Leu
1880                1885                1890                1895

GAG CAG ACA CAG CCG GCT GTG CTC CGA GGA GCC CGG GTT TTC CTT CGA         5824
Glu Gln Thr Gln Pro Ala Val Leu Arg Gly Ala Arg Val Phe Leu Arg
             1900                1905                1910

CAG AAG AGT TCC ACC TCC CTC AGC AAT GGC GGG GCC ATA CAA AAC CAA         5872
Gln Lys Ser Ser Thr Ser Leu Ser Asn Gly Gly Ala Ile Gln Asn Gln
             1915                1920                1925

GAG AGT GGC ATC AAA GAG TCT GTC TCC TGG GGC ACT CAA AGG ACC CAG         5920
Glu Ser Gly Ile Lys Glu Ser Val Ser Trp Gly Thr Gln Arg Thr Gln
             1930                1935                1940

GAT GCA CCC CAT GAG GCC AGG CCA CCC CTG GAG CGT GGC CAC TCC ACA         5968
Asp Ala Pro His Glu Ala Arg Pro Pro Leu Glu Arg Gly His Ser Thr
             1945                1950                1955

GAG ATC CCT GTG GGG CGG TCA GGA GCA CTG GCT GTG GAC GTT CAG ATG         6016
Glu Ile Pro Val Gly Arg Ser Gly Ala Leu Ala Val Asp Val Gln Met
1960                1965                1970                1975
```

```
CAG AGC ATA ACC CGG AGG GGC CCT GAT GGG GAG CCC CAG CCT GGG CTG     6064
Gln Ser Ile Thr Arg Arg Gly Pro Asp Gly Glu Pro Gln Pro Gly Leu
            1980                1985                1990

GAG AGC CAG GGT CGA GCG GCC TCC ATG CCC CGC CTT GCG GCC GAG ACT     6112
Glu Ser Gln Gly Arg Ala Ala Ser Met Pro Arg Leu Ala Ala Glu Thr
        1995                2000                2005

CAG CCC GTC ACA GAT GCC AGC CCC ATG AAG CGC TCC ATC TCC ACG CTG     6160
Gln Pro Val Thr Asp Ala Ser Pro Met Lys Arg Ser Ile Ser Thr Leu
2010                2015                2020

GCC CAG CGG CCC CGT GGG ACT CAT CTT TGC AGC ACC ACC CCG GAC CGC     6208
Ala Gln Arg Pro Arg Gly Thr His Leu Cys Ser Thr Thr Pro Asp Arg
            2025                2030                2035

CCA CCC CCT AGC CAG GCG TCG TCG CAC CAC CAC CAC CAC CGC TGC CAC     6256
Pro Pro Pro Ser Gln Ala Ser Ser His His His His His Arg Cys His
2040                2045                2050                2055

CGC CGC AGG GAC AGG AAG CAG AGG TCC CTG GAG AAG GGG CCC AGC CTG     6304
Arg Arg Arg Asp Arg Lys Gln Arg Ser Leu Glu Lys Gly Pro Ser Leu
            2060                2065                2070

TCT GCC GAT ATG GAT GGC GCA CCA AGC AGT GCT GTG GGG CCG GGG CTG     6352
Ser Ala Asp Met Asp Gly Ala Pro Ser Ser Ala Val Gly Pro Gly Leu
        2075                2080                2085

CCC CCG GGA GAG GGG CCT ACA GGC TGC CGG CGG GAA CGA GAG CGC CGG     6400
Pro Pro Gly Glu Gly Pro Thr Gly Cys Arg Arg Glu Arg Glu Arg Arg
    2090                2095                2100

CAG GAG CGG AGC CGG TCC CAG GAG CGG AGG CAG CCC TCA TCC TCC TCC     6448
Gln Glu Arg Ser Arg Ser Gln Glu Arg Arg Gln Pro Ser Ser Ser Ser
        2105                2110                2115

TCG GAG AAG CAG CGC TTC TAC TCC TGC GAC CGC TTT GGG GGC CGT GAG     6496
Ser Glu Lys Gln Arg Phe Tyr Ser Cys Asp Arg Phe Gly Gly Arg Glu
2120                2125                2130                2135

CCC CCG AAG CCC AAG CCC TCC CTC AGC AGC CAC CCA ACG TCG CCA ACA     6544
Pro Pro Lys Pro Lys Pro Ser Leu Ser Ser His Pro Thr Ser Pro Thr
            2140                2145                2150

GCT GGC CAG GAG CCG GGA CCC CAC CCA CAG GGC AGT GGT TCC GTG AAT     6592
Ala Gly Gln Glu Pro Gly Pro His Pro Gln Gly Ser Gly Ser Val Asn
        2155                2160                2165

GGG AGC CCC TTG CTG TCA ACA TCT GGT GCT AGC ACC CCC GGC CGC GGT     6640
Gly Ser Pro Leu Leu Ser Thr Ser Gly Ala Ser Thr Pro Gly Arg Gly
    2170                2175                2180

GGG CGG AGG CAG CTC CCC CAG ACG CCC CTG ACT CCC GCC CCC AGC ATC     6688
Gly Arg Arg Gln Leu Pro Gln Thr Pro Leu Thr Pro Arg Pro Ser Ile
2185                2190                2195

ACC TAC AAG ACG GCC AAC TCC TCA CCC ATC CAC TTC GCC GGG GCT CAG     6736
Thr Tyr Lys Thr Ala Asn Ser Ser Pro Ile His Phe Ala Gly Ala Gln
2200                2205                2210                2215

ACC AGC CTC CCT GCC TTC TCC CCA GGC CGG CTC AGC CGT GGG CTT TCC     6784
Thr Ser Leu Pro Ala Phe Ser Pro Gly Arg Leu Ser Arg Gly Leu Ser
            2220                2225                2230

GAA CAC AAC GCC CTG CTG CAG AGA GAC CCC CTC AGC CAG CCC CTG GCC     6832
Glu His Asn Ala Leu Leu Gln Arg Asp Pro Leu Ser Gln Pro Leu Ala
        2235                2240                2245

CCT GGC TCT CGA ATT GGC TCT GAC CCT TAC CTG GGG CAG CGT CTG GAC     6880
Pro Gly Ser Arg Ile Gly Ser Asp Pro Tyr Leu Gly Gln Arg Leu Asp
    2250                2255                2260

AGT GAG GCC TCT GTC CAC GCC CTG CCT GAG GAC ACG CTC ACT TTC GAG     6928
Ser Glu Ala Ser Val His Ala Leu Pro Glu Asp Thr Leu Thr Phe Glu
        2265                2270                2275

GAG GCT GTG GCC ACC AAC TCG GGC CGC TCC TCC AGG ACT TCC TAC GTG     6976
Glu Ala Val Ala Thr Asn Ser Gly Arg Ser Ser Arg Thr Ser Tyr Val
```

-continued

```
2280                2285                2290                2295
TCC TCC CTG ACC TCC CAG TCT CAC CCT CTC CGC CGC GTG CCC AAC GGT        7024
Ser Ser Leu Thr Ser Gln Ser His Pro Leu Arg Arg Val Pro Asn Gly
                2300                2305                2310

TAC CAC TGC ACC CTG GGA CTC AGC TCG GGT GGC CGA GCA CGG CAC AGC        7072
Tyr His Cys Thr Leu Gly Leu Ser Ser Gly Gly Arg Ala Arg His Ser
                2315                2320                2325

TAC CAC CAC CCT GAC CAA GAC CAC TGG TGC TAGCTGCACC GTGACCGCTC          7122
Tyr His His Pro Asp Gln Asp His Trp Cys
                2330                2335

AGACGCCTGC ATGCAGCAGG CGTGTGTTCC AGTGGATGAG TTTTATCATC CACACGGGGC      7182

AGTCGGCCCT CGGGGGAGGC CTTGCCCACC TTGGTGAGGC TCCTGTGGCC CCTCCCTCCC      7242

CCTCCTCCCC TCTTTTACTC TAGA                                            7266

(2) INFORMATION FOR SEQ ID NO:2:

(i) SEQUENCE CHARACTERISTICS:
        (A) LENGTH: 2337 amino acids
        (B) TYPE: amino acid
        (D) TOPOLOGY: linear (ii) MOLECULE TYPE: protein (xi) SEQUENCE DESCRIPTION: SEQ ID NO:2:

Met Val Arg Phe Gly Asp Glu Leu Gly Gly Arg Tyr Gly Gly Pro Gly
1               5                   10                  15

Ser Gly Glu Arg Ala Arg Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255
```

-continued

```
Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
            275                 280                 285

Gly Pro Asn Phe Gly Ile Thr Asn Phe Asp Asn Ile Leu Phe Ala Ile
            290                 295                 300

Leu Thr Val Phe Gln Cys Ile Thr Met Glu Gly Trp Thr Asp Ile Leu
305                     310                 315                 320

Tyr Asn Thr Asn Asp Ala Ala Gly Asn Thr Trp Asn Trp Leu Tyr Phe
                    325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
            355                 360                 365

Arg Arg Ala Phe Leu Lys Leu Arg Arg Gln Gln Gln Ile Glu Arg Glu
            370                 375                 380

Leu Asn Gly Tyr Leu Glu Trp Ile Phe Lys Ala Glu Glu Val Met Leu
385                     390                 395                 400

Ala Glu Glu Asp Arg Asn Ala Glu Glu Lys Ser Pro Leu Asp Val Leu
                    405                 410                 415

Lys Arg Ala Ala Thr Lys Lys Ser Arg Asn Asp Leu Ile His Ala Glu
                    420                 425                 430

Glu Gly Glu Asp Arg Phe Ala Asp Leu Cys Ala Val Gly Ser Pro Phe
            435                 440                 445

Ala Arg Ala Ser Leu Lys Ser Gly Lys Thr Glu Ser Ser Ser Tyr Phe
            450                 455                 460

Arg Arg Lys Glu Lys Met Phe Arg Phe Phe Ile Arg Arg Met Val Lys
465                     470                 475                 480

Ala Gln Ser Phe Tyr Trp Val Val Leu Cys Val Val Ala Leu Asn Thr
                    485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
            515                 520                 525

Met Ser Leu Lys Met Tyr Gly Leu Gly Pro Arg Ser Tyr Phe Arg Ser
            530                 535                 540

Ser Phe Asn Cys Phe Asp Phe Gly Val Ile Val Gly Ser Val Phe Glu
545                     550                 555                 560

Val Val Trp Ala Ala Ile Lys Pro Gly Ser Ser Phe Gly Ile Ser Val
                    565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
            595                 600                 605

Ile Ile Ser Leu Leu Phe Leu Leu Phe Leu Phe Ile Val Val Phe Ala
            610                 615                 620

Leu Leu Gly Met Gln Leu Phe Gly Gly Gln Phe Asn Phe Gln Asp Glu
625                     630                 635                 640

Thr Pro Thr Thr Asn Phe Asp Thr Phe Pro Ala Ala Ile Leu Thr Val
                    645                 650                 655

Phe Gln Ile Leu Thr Gly Glu Asp Trp Asn Ala Val Met Tyr His Gly
            660                 665                 670
```

-continued

Ile Glu Ser Gln Gly Gly Val Ser Lys Gly Met Phe Ser Ser Phe Tyr
             675                 680                 685

Phe Ile Val Leu Thr Leu Phe Gly Asn Tyr Thr Leu Leu Asn Val Phe
         690                 695                 700

Leu Ala Ile Ala Val Asp Asn Leu Ala Asn Ala Gln Glu Leu Thr Lys
705                 710                 715                 720

Asp Glu Glu Met Glu Glu Ala Ala Asn Gln Lys Leu Ala Leu Gln
                 725                 730                 735

Lys Ala Lys Glu Val Ala Glu Val Ser Pro Met Ser Ala Ala Asn Ile
             740                 745                 750

Ser Ile Ala Ala Arg Gln Gln Asn Ser Ala Lys Ala Arg Ser Val Trp
         755                 760                 765

Glu Gln Arg Ala Ser Gln Leu Arg Leu Gln Asn Leu Arg Ala Ser Cys
         770                 775                 780

Glu Ala Leu Tyr Ser Glu Met Asp Pro Glu Glu Arg Leu Arg Phe Ala
785                 790                 795                 800

Thr Thr Arg His Arg Arg Pro Asp Met Lys Thr His Leu Asp Arg Pro
                 805                 810                 815

Leu Val Val Glu Leu Gly Arg Asp Gly Ala Arg Gly Pro Val Gly Gly
             820                 825                 830

Lys Ala Arg Pro Glu Ala Ala Glu Ala Pro Gly Val Asp Pro Pro
         835                 840                 845

Arg Arg His His Arg His Arg Asp Lys Asp Lys Thr Pro Ala Ala Gly
850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                 885                 890                 895

Ala Gly Pro Pro Glu Ala Arg Ser Glu Arg Gly Arg Gly Pro Gly Pro
             900                 905                 910

Glu Gly Gly Arg Arg His His Arg Arg Gly Ser Pro Glu Glu Ala Ala
         915                 920                 925

Glu Arg Glu Pro Arg Arg His Arg Ala His Arg His Gln Asp Pro Ser
930                 935                 940

Lys Glu Cys Ala Gly Ala Lys Gly Glu Arg Ala Arg His Arg Gly
945                 950                 955                 960

Gly Pro Arg Ala Gly Pro Arg Glu Ala Glu Ser Gly Glu Glu Pro Ala
                 965                 970                 975

Arg Arg His Arg Ala Arg His Lys Ala Gln Pro Ala His Glu Ala Val
             980                 985                 990

Glu Lys Glu Thr Thr Glu Lys Glu Ala Thr Glu Lys Glu Ala Glu Ile
         995                 1000                1005

Val Glu Ala Asp Lys Glu Lys Glu Leu Arg Asn His Gln Pro Arg Glu
    1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Pro Glu
                 1045                1050                1055

Asp Ala Asp Asn Gln Arg Asn Val Thr Arg Met Gly Ser Gln Pro Pro
             1060                1065                1070

Asp Pro Asn Thr Ile Val His Ile Pro Val Met Leu Thr Gly Pro Leu
         1075                1080                1085

Gly Glu Ala Thr Val Val Pro Ser Gly Asn Val Asp Leu Glu Ser Gln

-continued

```
        1090                1095                1100
Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
                1125                1130                1135

Asn Leu Leu Arg Arg Phe Cys His Tyr Ile Val Thr Met Arg Tyr Phe
                1140                1145                1150

Glu Val Val Ile Leu Val Val Ile Ala Leu Ser Ser Ile Ala Leu Ala
                1155                1160                1165

Ala Glu Asp Pro Val Arg Thr Asp Ser Pro Arg Asn Asn Ala Leu Lys
                1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu His Pro Gly Ala Tyr Phe Arg
                1205                1210                1215

Asp Leu Trp Asn Ile Leu Asp Phe Ile Val Val Ser Gly Ala Leu Val
                1220                1225                1230

Ala Phe Ala Phe Ser Gly Ser Lys Gly Lys Asp Ile Asn Thr Ile Lys
                1235                1240                1245

Ser Leu Arg Val Leu Arg Val Leu Arg Pro Leu Lys Thr Ile Lys Arg
                1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
                1285                1290                1295

Ala Val Ile Ala Val Gln Leu Phe Lys Gly Lys Phe Phe Tyr Cys Thr
                1300                1305                1310

Asp Glu Ser Lys Glu Leu Glu Arg Asp Cys Arg Gly Gln Tyr Leu Asp
                1315                1320                1325

Tyr Glu Lys Glu Glu Val Glu Ala Gln Pro Arg Gln Trp Lys Lys Tyr
                1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
                1365                1370                1375

Ala Thr Tyr Glu Glu Gln Gly Pro Ser Pro Gly Tyr Arg Met Glu Leu
                1380                1385                1390

Ser Ile Phe Tyr Val Val Tyr Phe Val Val Phe Pro Phe Phe Phe Val
                1395                1400                1405

Asn Ile Phe Val Ala Leu Ile Ile Ile Thr Phe Gln Glu Gln Gly Asp
                1410                1415                1420

Lys Val Met Ser Glu Cys Ser Leu Glu Lys Asn Glu Arg Ala Cys Ile
1425                1430                1435                1440

Asp Phe Ala Ile Ser Ala Lys Pro Leu Thr Arg Tyr Met Pro Gln Asn
                1445                1450                1455

Arg Gln Ser Phe Gln Tyr Lys Thr Trp Thr Phe Val Val Ser Pro Pro
                1460                1465                1470

Phe Glu Tyr Phe Ile Met Ala Met Ile Ala Leu Asn Thr Val Val Leu
                1475                1480                1485

Met Met Lys Phe Tyr Asp Ala Pro Tyr Glu Tyr Glu Leu Met Leu Lys
                1490                1495                1500

Cys Leu Asn Ile Val Phe Thr Ser Met Phe Ser Met Glu Cys Val Leu
1505                1510                1515                1520
```

-continued

```
Lys Ile Ile Ala Phe Gly Val Leu Asn Tyr Phe Arg Asp Ala Trp Asn
            1525                1530                1535

Val Phe Asp Phe Val Thr Val Leu Gly Ser Ile Thr Asp Ile Leu Val
            1540                1545                1550

Thr Glu Ile Ala Asn Asn Phe Ile Asn Leu Ser Phe Leu Arg Leu Phe
            1555                1560                1565

Arg Ala Ala Arg Leu Ile Lys Leu Leu Arg Gln Gly Tyr Thr Ile Arg
            1570                1575                1580

Ile Leu Leu Trp Thr Phe Val Gln Ser Phe Lys Ala Leu Pro Tyr Val
1585                1590                1595                1600

Cys Leu Leu Ile Ala Met Leu Phe Phe Ile Tyr Ala Ile Ile Gly Met
            1605                1610                1615

Gln Val Phe Gly Asn Ile Ala Leu Asp Asp Asp Thr Ser Ile Asn Arg
            1620                1625                1630

His Asn Asn Phe Arg Thr Phe Leu Gln Ala Leu Met Leu Leu Phe Arg
            1635                1640                1645

Ser Ala Thr Gly Glu Ala Trp His Glu Ile Met Leu Ser Cys Leu Ser
            1650                1655                1660

Asn Gln Ala Cys Asp Glu Gln Ala Asn Ala Thr Glu Cys Gly Ser Asp
1665                1670                1675                1680

Phe Ala Tyr Phe Tyr Phe Val Ser Phe Ile Phe Leu Cys Ser Phe Leu
            1685                1690                1695

Met Leu Asn Leu Phe Val Ala Val Ile Met Asp Asn Phe Glu Tyr Leu
            1700                1705                1710

Thr Arg Asp Ser Ser Ile Leu Gly Pro His His Leu Asp Glu Phe Ile
            1715                1720                1725

Arg Val Trp Ala Glu Tyr Asp Pro Ala Ala Cys Gly Arg Ile Ser Tyr
            1730                1735                1740

Asn Asp Met Phe Glu Met Leu Lys His Met Ser Pro Pro Leu Gly Leu
1745                1750                1755                1760

Gly Lys Lys Cys Pro Ala Arg Val Ala Tyr Lys Arg Leu Val Arg Met
            1765                1770                1775

Asn Met Pro Ile Ser Asn Glu Asp Met Thr Val His Phe Thr Ser Thr
            1780                1785                1790

Leu Met Ala Leu Ile Arg Thr Ala Leu Glu Ile Lys Leu Ala Pro Ala
            1795                1800                1805

Gly Thr Lys Gln His Gln Cys Asp Ala Glu Leu Arg Lys Glu Ile Ser
            1810                1815                1820

Val Val Trp Ala Asn Leu Pro Gln Lys Thr Leu Asp Leu Leu Val Pro
1825                1830                1835                1840

Pro His Lys Pro Asp Glu Met Thr Val Gly Lys Val Tyr Ala Ala Leu
            1845                1850                1855

Met Ile Phe Asp Phe Tyr Lys Gln Asn Lys Thr Thr Arg Asp Gln Met
            1860                1865                1870

Gln Gln Ala Pro Gly Gly Leu Ser Gln Met Gly Pro Val Ser Leu Phe
            1875                1880                1885

His Pro Leu Lys Ala Thr Leu Glu Gln Thr Gln Pro Ala Val Leu Arg
            1890                1895                1900

Gly Ala Arg Val Phe Leu Arg Gln Lys Ser Ser Thr Ser Leu Ser Asn
1905                1910                1915                1920

Gly Gly Ala Ile Gln Asn Gln Glu Ser Gly Ile Lys Glu Ser Val Ser
            1925                1930                1935
```

```
Trp Gly Thr Gln Arg Thr Gln Asp Ala Pro His Glu Ala Arg Pro Pro
            1940                1945                1950

Leu Glu Arg Gly His Ser Thr Glu Ile Pro Val Gly Arg Ser Gly Ala
        1955                1960                1965

Leu Ala Val Asp Val Gln Met Gln Ser Ile Thr Arg Arg Gly Pro Asp
    1970                1975                1980

Gly Glu Pro Gln Pro Gly Leu Ser Gln Gly Arg Ala Ala Ser Met
1985                1990                1995                2000

Pro Arg Leu Ala Ala Glu Thr Gln Pro Val Thr Asp Ala Ser Pro Met
                2005                2010                2015

Lys Arg Ser Ile Ser Thr Leu Ala Gln Arg Pro Arg Gly Thr His Leu
            2020                2025                2030

Cys Ser Thr Thr Pro Asp Arg Pro Pro Ser Gln Ala Ser Ser His
        2035                2040                2045

His His His His Arg Cys His Arg Arg Asp Arg Lys Gln Arg Ser
    2050                2055                2060

Leu Glu Lys Gly Pro Ser Leu Ser Ala Asp Met Asp Gly Ala Pro Ser
2065                2070                2075                2080

Ser Ala Val Gly Pro Gly Leu Pro Pro Gly Glu Gly Pro Thr Gly Cys
                2085                2090                2095

Arg Arg Glu Arg Glu Arg Arg Gln Glu Arg Ser Arg Ser Gln Glu Arg
            2100                2105                2110

Arg Gln Pro Ser Ser Ser Ser Ser Glu Lys Gln Arg Phe Tyr Ser Cys
        2115                2120                2125

Asp Arg Phe Gly Gly Arg Glu Pro Pro Lys Pro Lys Pro Ser Leu Ser
    2130                2135                2140

Ser His Pro Thr Ser Pro Thr Ala Gly Gln Glu Pro Gly Pro His Pro
2145                2150                2155                2160

Gln Gly Ser Gly Ser Val Asn Gly Ser Pro Leu Leu Ser Thr Ser Gly
                2165                2170                2175

Ala Ser Thr Pro Gly Arg Gly Gly Arg Arg Gln Leu Pro Gln Thr Pro
            2180                2185                2190

Leu Thr Pro Arg Pro Ser Ile Thr Tyr Lys Thr Ala Asn Ser Ser Pro
        2195                2200                2205

Ile His Phe Ala Gly Ala Gln Thr Ser Leu Pro Ala Phe Ser Pro Gly
    2210                2215                2220

Arg Leu Ser Arg Gly Leu Ser Glu His Asn Ala Leu Leu Gln Arg Asp
2225                2230                2235                2240

Pro Leu Ser Gln Pro Leu Ala Pro Gly Ser Arg Ile Gly Ser Asp Pro
                2245                2250                2255

Tyr Leu Gly Gln Arg Leu Asp Ser Glu Ala Ser Val His Ala Leu Pro
            2260                2265                2270

Glu Asp Thr Leu Thr Phe Glu Glu Ala Val Ala Thr Asn Ser Gly Arg
        2275                2280                2285

Ser Ser Arg Thr Ser Tyr Val Ser Ser Leu Thr Ser Gln Ser His Pro
    2290                2295                2300

Leu Arg Arg Val Pro Asn Gly Tyr His Cys Thr Leu Gly Leu Ser Ser
2305                2310                2315                2320

Gly Gly Arg Ala Arg His Ser Tyr His His Pro Asp Gln Asp His Trp
                2325                2330                2335

Cys (2) INFORMATION FOR SEQ ID NO:3:
```

(i) SEQUENCE CHARACTERISTICS:
    (A) LENGTH: 3298 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 20..3292

(xi) SEQUENCE DESCRIPTION: SEQ ID NO:3:

```
TTGATCTTCG ATCGCGAAG ATG GCT GCT GGC TGC CTG CTG GCC TTG ACT CTG         52
                     Met Ala Ala Gly Cys Leu Leu Ala Leu Thr Leu
                         2340                    2345

ACA CTT TTC CAA TCT TTG CTC ATC GGC CCC TCG TCG GAG GAG CCG TTC         100
Thr Leu Phe Gln Ser Leu Leu Ile Gly Pro Ser Ser Glu Glu Pro Phe
    2350                2355                2360

CCT TCG GCC GTC ACT ATC AAA TCA TGG GTG GAT AAG ATG CAA GAA GAC         148
Pro Ser Ala Val Thr Ile Lys Ser Trp Val Asp Lys Met Gln Glu Asp
2365            2370                2375                2380

CTT GTC ACA CTG GCA AAA ACA GCA AGT GGA GTC AAT CAG CTT GTT GAT         196
Leu Val Thr Leu Ala Lys Thr Ala Ser Gly Val Asn Gln Leu Val Asp
                2385                2390                2395

ATT TAT GAG AAA TAT CAA GAT TTG TAT ACT GTG GAA CCA AAT AAT GCA         244
Ile Tyr Glu Lys Tyr Gln Asp Leu Tyr Thr Val Glu Pro Asn Asn Ala
            2400                2405                2410

CGC CAG CTG GTA GAA ATT GCA GCC AGG GAT ATT GAG AAA CTT CTG AGC         292
Arg Gln Leu Val Glu Ile Ala Ala Arg Asp Ile Glu Lys Leu Leu Ser
        2415                2420                2425

AAC AGA TCT AAA GCC CTG GTG AGC CTG GCA TTG GAA GCG GAG AAA GTT         340
Asn Arg Ser Lys Ala Leu Val Ser Leu Ala Leu Glu Ala Glu Lys Val
    2430                2435                2440

CAA GCA GCT CAC CAG TGG AGA GAA GAT TTT GCA AGC AAT GAA GTT GTC         388
Gln Ala Ala His Gln Trp Arg Glu Asp Phe Ala Ser Asn Glu Val Val
2445            2450                2455                2460

TAC TAC AAT GCA AAG GAT GAT CTC GAT CCT GAG AAA AAT GAC AGT GAG         436
Tyr Tyr Asn Ala Lys Asp Asp Leu Asp Pro Glu Lys Asn Asp Ser Glu
                2465                2470                2475

CCA GGC AGC CAG AGG ATA AAA CCT GTT TTC ATT GAA GAT GCT AAT TTT         484
Pro Gly Ser Gln Arg Ile Lys Pro Val Phe Ile Glu Asp Ala Asn Phe
            2480                2485                2490

GGA CGA CAA ATA TCT TAT CAG CAC GCA GCA GTC CAT ATT CCT ACT GAC         532
Gly Arg Gln Ile Ser Tyr Gln His Ala Ala Val His Ile Pro Thr Asp
        2495                2500                2505

ATC TAT GAG GGC TCA ACA ATT GTG TTA AAT GAA CTC AAC TGG ACA AGT         580
Ile Tyr Glu Gly Ser Thr Ile Val Leu Asn Glu Leu Asn Trp Thr Ser
    2510                2515                2520

GCC TTA GAT GAA GTT TTC AAA AAG AAT CGC GAG GAA GAC CCT TCA TTA         628
Ala Leu Asp Glu Val Phe Lys Lys Asn Arg Glu Glu Asp Pro Ser Leu
2525            2530                2535                2540

TTG TGG CAG GTT TTT GGC AGT GCC ACT GGC CTA GCT CGA TAT TAT CCA         676
Leu Trp Gln Val Phe Gly Ser Ala Thr Gly Leu Ala Arg Tyr Tyr Pro
                2545                2550                2555

GCT TCA CCA TGG GTT GAT AAT AGT AGA ACT CCA AAT AAG ATT GAC CTT         724
Ala Ser Pro Trp Val Asp Asn Ser Arg Thr Pro Asn Lys Ile Asp Leu
            2560                2565                2570

TAT GAT GTA CGC AGA AGA CCA TGG TAC ATC CAA GGA GCT GCA TCT CCT         772
Tyr Asp Val Arg Arg Arg Pro Trp Tyr Ile Gln Gly Ala Ala Ser Pro
        2575                2580                2585
```

```
AAA GAC ATG CTT ATT CTG GTG GAT GTG AGT GGA AGT GTT AGT GGA TTG        820
Lys Asp Met Leu Ile Leu Val Asp Val Ser Gly Ser Val Ser Gly Leu
2590            2595            2600

ACA CTT AAA CTG ATC CGA ACA TCT GTC TCC GAA ATG TTA GAA ACC CTC        868
Thr Leu Lys Leu Ile Arg Thr Ser Val Ser Glu Met Leu Glu Thr Leu
2605            2610            2615            2620

TCA GAT GAT GAT TTC GTG AAT GTA GCT TCA TTT AAC AGC AAT GCT CAG        916
Ser Asp Asp Asp Phe Val Asn Val Ala Ser Phe Asn Ser Asn Ala Gln
                2625            2630            2635

GAT GTA AGC TGT TTT CAG CAC CTT GTC CAA GCA AAT GTA AGA AAT AAA        964
Asp Val Ser Cys Phe Gln His Leu Val Gln Ala Asn Val Arg Asn Lys
    2640            2645            2650

AAA GTG TTG AAA GAC GCG GTG AAT AAT ATC ACA GCC AAA GGA ATT ACA       1012
Lys Val Leu Lys Asp Ala Val Asn Asn Ile Thr Ala Lys Gly Ile Thr
2655            2660            2665

GAT TAT AAG AAG GGC TTT AGT TTT GCT TTT GAA CAG CTG CTT AAT TAT       1060
Asp Tyr Lys Lys Gly Phe Ser Phe Ala Phe Glu Gln Leu Leu Asn Tyr
        2670            2675            2680

AAT GTT TCC AGA GCA AAC TGC AAT AAG ATT ATT ATG CTA TTC ACG GAT       1108
Asn Val Ser Arg Ala Asn Cys Asn Lys Ile Ile Met Leu Phe Thr Asp
2685            2690            2695            2700

GGA GGA GAA GAG AGA GCC CAG GAG ATA TTT AAC AAA TAC AAT AAA GAT       1156
Gly Gly Glu Glu Arg Ala Gln Glu Ile Phe Asn Lys Tyr Asn Lys Asp
            2705            2710            2715

AAA AAA GTA CGT GTA TTC AGG TTT TCA GTT GGT CAA CAC AAT TAT GAG       1204
Lys Lys Val Arg Val Phe Arg Phe Ser Val Gly Gln His Asn Tyr Glu
        2720            2725            2730

AGA GGA CCT ATT CAG TGG ATG GCC TGT GAA AAC AAA GGT TAT TAT TAT       1252
Arg Gly Pro Ile Gln Trp Met Ala Cys Glu Asn Lys Gly Tyr Tyr Tyr
            2735            2740            2745

GAA ATT CCT TCC ATT GGT GCA ATA AGA ATC AAT ACT CAG GAA TAT TTG       1300
Glu Ile Pro Ser Ile Gly Ala Ile Arg Ile Asn Thr Gln Glu Tyr Leu
        2750            2755            2760

GAT GTT TTG GGA AGA CCA ATG GTT TTA GCA GGA GAC AAA GCT AAG CAA       1348
Asp Val Leu Gly Arg Pro Met Val Leu Ala Gly Asp Lys Ala Lys Gln
2765            2770            2775            2780

GTC CAA TGG ACA AAT GTG TAC CTG GAT GCA TTG GAA CTG GGA CTT GTC       1396
Val Gln Trp Thr Asn Val Tyr Leu Asp Ala Leu Glu Leu Gly Leu Val
            2785            2790            2795

ATT ACT GGA ACT CTT CCG GTC TTC AAC ATA ACC GGC CAA TTT GAA AAT       1444
Ile Thr Gly Thr Leu Pro Val Phe Asn Ile Thr Gly Gln Phe Glu Asn
        2800            2805            2810

AAG ACA AAC TTA AAG AAC CAG CTG ATT CTT GGT GTG ATG GGA GTA GAT       1492
Lys Thr Asn Leu Lys Asn Gln Leu Ile Leu Gly Val Met Gly Val Asp
            2815            2820            2825

GTG TCT TTG GAA GAT ATT AAA AGA CTG ACA CCA CGT TTT ACA CTG TGC       1540
Val Ser Leu Glu Asp Ile Lys Arg Leu Thr Pro Arg Phe Thr Leu Cys
2830            2835            2840

CCC AAT GGG TAT TAC TTT GCA ATC GAT CCT AAT GGT TAT GCT TTA TTA       1588
Pro Asn Gly Tyr Tyr Phe Ala Ile Asp Pro Asn Gly Tyr Ala Leu Leu
2845            2850            2855            2860

CAT CCA AAT CTT CAG CCA AAG AAC CCC AAA TCT CAG GAG CCA GTA ACA       1636
His Pro Asn Leu Gln Pro Lys Asn Pro Lys Ser Gln Glu Pro Val Thr
            2865            2870            2875

TTG GAT TTC CTT GAT GCA GAG TTA GAG AAT GAT ATT AAA GTG GAG ATT       1684
Leu Asp Phe Leu Asp Ala Glu Leu Glu Asn Asp Ile Lys Val Glu Ile
        2880            2885            2890

CGA AAT AAG ATG ATT GAT GGG GAA AGT GGA GAA AAA ACA TTC AGA ACT       1732
Arg Asn Lys Met Ile Asp Gly Glu Ser Gly Glu Lys Thr Phe Arg Thr
            2895            2900            2905
```

```
CTG GTT AAA TCT CAA GAT GAG AGA TAT ATT GAC AAA GGA AAC AGG ACA    1780
Leu Val Lys Ser Gln Asp Glu Arg Tyr Ile Asp Lys Gly Asn Arg Thr
    2910                2915                2920

TAC ACA TGG ACA CCT GTC AAT GGC ACA GAT TAC AGT TTG GCC TTG GTA    1828
Tyr Thr Trp Thr Pro Val Asn Gly Thr Asp Tyr Ser Leu Ala Leu Val
2925                2930                2935                2940

TTA CCA ACC TAC AGT TTT TAC TAT ATA AAA GCC AAA CTA GAA GAG ACA    1876
Leu Pro Thr Tyr Ser Phe Tyr Tyr Ile Lys Ala Lys Leu Glu Glu Thr
        2945                2950                2955

ATA ACT CAG GCC AGA TCA AAA AAG GGC AAA ATG AAG GAT TCG GAA ACC    1924
Ile Thr Gln Ala Arg Ser Lys Lys Gly Lys Met Lys Asp Ser Glu Thr
            2960                2965                2970

CTG AAG CCA GAT AAT TTT GAA GAA TCT GGC TAT ACA TTC ATA GCA CCA    1972
Leu Lys Pro Asp Asn Phe Glu Glu Ser Gly Tyr Thr Phe Ile Ala Pro
                2975                2980                2985

AGA GAT TAC TGC AAT GAC CTG AAA ATA TCG GAT AAT AAC ACT GAA TTT    2020
Arg Asp Tyr Cys Asn Asp Leu Lys Ile Ser Asp Asn Asn Thr Glu Phe
                    2990                2995                3000

CTT TTA AAT TTC AAC GAG TTT ATT GAT AGA AAA ACT CCA AAC AAC CCA    2068
Leu Leu Asn Phe Asn Glu Phe Ile Asp Arg Lys Thr Pro Asn Asn Pro
3005                3010                3015                3020

TCA TGT AAC GCG GAT TTG ATT AAT AGA GTC TTG CTT GAT GCA GGC TTT    2116
Ser Cys Asn Ala Asp Leu Ile Asn Arg Val Leu Leu Asp Ala Gly Phe
        3025                3030                3035

ACA AAT GAA CTT GTC CAA AAT TAC TGG AGT AAG CAG AAA AAT ATC AAG    2164
Thr Asn Glu Leu Val Gln Asn Tyr Trp Ser Lys Gln Lys Asn Ile Lys
            3040                3045                3050

GGA GTG AAA GCA CGA TTT GTT GTG ACT GAT GGT GGG ATT ACC AGA GTT    2212
Gly Val Lys Ala Arg Phe Val Val Thr Asp Gly Gly Ile Thr Arg Val
                3055                3060                3065

TAT CCC AAA GAG GCT GGA GAA AAT TGG CAA GAA AAC CCA GAG ACA TAT    2260
Tyr Pro Lys Glu Ala Gly Glu Asn Trp Gln Glu Asn Pro Glu Thr Tyr
                    3070                3075                3080

GAG GAC AGC TTC TAT AAA AGG AGC CTA GAT AAT GAT AAC TAT GTT TTC    2308
Glu Asp Ser Phe Tyr Lys Arg Ser Leu Asp Asn Asp Asn Tyr Val Phe
3085                3090                3095                3100

ACT GCT CCC TAC TTT AAC AAA AGT GGA CCT GGT GCC TAT GAA TCG GGC    2356
Thr Ala Pro Tyr Phe Asn Lys Ser Gly Pro Gly Ala Tyr Glu Ser Gly
        3105                3110                3115

ATT ATG GTA AGC AAA GCT GTA GAA ATA TAT ATT CAA GGG AAA CTT CTT    2404
Ile Met Val Ser Lys Ala Val Glu Ile Tyr Ile Gln Gly Lys Leu Leu
            3120                3125                3130

AAA CCT GCA GTT GTT GGA ATT AAA ATT GAT GTA AAT TCC TGG ATA GAG    2452
Lys Pro Ala Val Val Gly Ile Lys Ile Asp Val Asn Ser Trp Ile Glu
                3135                3140                3145

AAT TTC ACC AAA ACC TCA ATC AGA GAT CCG TGT GCT GGT CCA GTT TGT    2500
Asn Phe Thr Lys Thr Ser Ile Arg Asp Pro Cys Ala Gly Pro Val Cys
                    3150                3155                3160

GAC TGC AAA AGA AAC AGT GAC GTA ATG GAT TGT GTG ATT CTG GAT GAT    2548
Asp Cys Lys Arg Asn Ser Asp Val Met Asp Cys Val Ile Leu Asp Asp
3165                3170                3175                3180

GGT GGG TTT CTT CTG ATG GCA AAT CAT GAT GAT TAT ACT AAT CAG ATT    2596
Gly Gly Phe Leu Leu Met Ala Asn His Asp Asp Tyr Thr Asn Gln Ile
        3185                3190                3195

GGA AGA TTT TTT GGA GAG ATT GAT CCC AGC TTG ATG AGA CAC CTG GTT    2644
Gly Arg Phe Phe Gly Glu Ile Asp Pro Ser Leu Met Arg His Leu Val
            3200                3205                3210

AAT ATA TCA GTT TAT GCT TTT AAC AAA TCT TAT GAT TAT CAG TCA GTA    2692
Asn Ile Ser Val Tyr Ala Phe Asn Lys Ser Tyr Asp Tyr Gln Ser Val
```

-continued

```
               3215                3220                3225
TGT GAG CCC GGT GCT GCA CCA AAA CAA GGA GCA GGA CAT CGC TCA GCA        2740
Cys Glu Pro Gly Ala Ala Pro Lys Gln Gly Ala Gly His Arg Ser Ala
        3230                3235                3240

TAT GTG CCA TCA GTA GCA GAC ATA TTA CAA ATT GGC TGG TGG GCC ACT        2788
Tyr Val Pro Ser Val Ala Asp Ile Leu Gln Ile Gly Trp Trp Ala Thr
3245                3250                3255                3260

GCT GCT GCC TGG TCT ATT CTA CAG CAG TTT CTC TTG AGT TTG ACC TTT        2836
Ala Ala Ala Trp Ser Ile Leu Gln Gln Phe Leu Leu Ser Leu Thr Phe
                3265                3270                3275

CCA CGA CTC CTT GAG GCA GTT GAG ATG GAG GAT GAT GAC TTC ACG GCC        2884
Pro Arg Leu Leu Glu Ala Val Glu Met Glu Asp Asp Asp Phe Thr Ala
        3280                3285                3290

TCC CTG TCC AAG CAG AGC TGC ATT ACT GAA CAA ACC CAG TAT TTC TTC        2932
Ser Leu Ser Lys Gln Ser Cys Ile Thr Glu Gln Thr Gln Tyr Phe Phe
        3295                3300                3305

GAT AAC GAC AGT AAA TCA TTC AGT GGT GTA TTA GAC TGT GGA AAC TGT        2980
Asp Asn Asp Ser Lys Ser Phe Ser Gly Val Leu Asp Cys Gly Asn Cys
        3310                3315                3320

TCC AGA ATC TTT CAT GGA GAA AAG CTT ATG AAC ACC AAC TTA ATA TTC        3028
Ser Arg Ile Phe His Gly Glu Lys Leu Met Asn Thr Asn Leu Ile Phe
3325                3330                3335                3340

ATA ATG GTT GAG AGC AAA GGG ACA TGT CCA TGT GAC ACA CGA CTG CTC        3076
Ile Met Val Glu Ser Lys Gly Thr Cys Pro Cys Asp Thr Arg Leu Leu
        3345                3350                3355

ATA CAA GCG GAG CAG ACT TCT GAC GGT CCA AAT CCT TGT GAC ATG GTT        3124
Ile Gln Ala Glu Gln Thr Ser Asp Gly Pro Asn Pro Cys Asp Met Val
        3360                3365                3370

AAG CAA CCT AGA TAC CGA AAA GGG CCT GAT GTC TGC TTT GAT AAC AAT        3172
Lys Gln Pro Arg Tyr Arg Lys Gly Pro Asp Val Cys Phe Asp Asn Asn
        3375                3380                3385

GTC TTG GAG GAT TAT ACT GAC TGT GGT GGT GTT TCT GGA TTA AAT CCC        3220
Val Leu Glu Asp Tyr Thr Asp Cys Gly Gly Val Ser Gly Leu Asn Pro
        3390                3395                3400

TCC CTG TGG TAT ATC ATT GGA ATC CAG TTT CTA CTA CTT TGG CTG GTA        3268
Ser Leu Trp Tyr Ile Ile Gly Ile Gln Phe Leu Leu Leu Trp Leu Val
3405                3410                3415                3420

TCT GGC AGC ACA CAC CGG CTG TTA TGACCT                                 3298
Ser Gly Ser Thr His Arg Leu Leu
                3425

(2) INFORMATION FOR SEQ ID NO:4:

(i) SEQUENCE CHARACTERISTICS:
        (A) LENGTH: 1091 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Ala Gly Cys Leu Leu Ala Leu Thr Leu Thr Leu Phe Gln Ser
  1               5                  10                  15

Leu Leu Ile Gly Pro Ser Ser Glu Glu Pro Phe Pro Ser Ala Val Thr
                 20                  25                  30

Ile Lys Ser Trp Val Asp Lys Met Gln Glu Asp Leu Val Thr Leu Ala
             35                  40                  45

Lys Thr Ala Ser Gly Val Asn Gln Leu Val Asp Ile Tyr Glu Lys Tyr
         50                  55                  60

Gln Asp Leu Tyr Thr Val Glu Pro Asn Asn Ala Arg Gln Leu Val Glu
```

```
              65                  70                  75                  80
     Ile Ala Ala Arg Asp Ile Glu Lys Leu Leu Ser Asn Arg Ser Lys Ala
                         85                  90                  95

Leu Val Ser Leu Ala Leu Glu Ala Glu Lys Val Gln Ala Ala His Gln
                    100                 105                 110

Trp Arg Glu Asp Phe Ala Ser Asn Glu Val Val Tyr Tyr Asn Ala Lys
                    115                 120                 125

Asp Asp Leu Asp Pro Glu Lys Asn Asp Ser Glu Pro Gly Ser Gln Arg
     130                 135                 140

Ile Lys Pro Val Phe Ile Glu Asp Ala Asn Phe Gly Arg Gln Ile Ser
     145                 150                 155                 160

Tyr Gln His Ala Ala Val His Ile Pro Thr Asp Ile Tyr Glu Gly Ser
                    165                 170                 175

Thr Ile Val Leu Asn Glu Leu Asn Trp Thr Ser Ala Leu Asp Glu Val
                    180                 185                 190

Phe Lys Lys Asn Arg Glu Glu Asp Pro Ser Leu Leu Trp Gln Val Phe
                    195                 200                 205

Gly Ser Ala Thr Gly Leu Ala Arg Tyr Tyr Pro Ala Ser Pro Trp Val
                    210                 215                 220

Asp Asn Ser Arg Thr Pro Asn Lys Ile Asp Leu Tyr Asp Val Arg Arg
     225                 230                 235                 240

Arg Pro Trp Tyr Ile Gln Gly Ala Ala Ser Pro Lys Asp Met Leu Ile
                    245                 250                 255

Leu Val Asp Val Ser Gly Ser Val Ser Gly Leu Thr Leu Lys Leu Ile
                    260                 265                 270

Arg Thr Ser Val Ser Glu Met Leu Glu Thr Leu Ser Asp Asp Asp Phe
                    275                 280                 285

Val Asn Val Ala Ser Phe Asn Ser Asn Ala Gln Asp Val Ser Cys Phe
     290                 295                 300

Gln His Leu Val Gln Ala Asn Val Arg Asn Lys Lys Val Leu Lys Asp
     305                 310                 315                 320

Ala Val Asn Asn Ile Thr Ala Lys Gly Ile Thr Asp Tyr Lys Lys Gly
                    325                 330                 335

Phe Ser Phe Ala Phe Glu Gln Leu Leu Asn Tyr Asn Val Ser Arg Ala
                    340                 345                 350

Asn Cys Asn Lys Ile Ile Met Leu Phe Thr Asp Gly Gly Glu Glu Arg
                    355                 360                 365

Ala Gln Glu Ile Phe Asn Lys Tyr Asn Lys Asp Lys Lys Val Arg Val
     370                 375                 380

Phe Arg Phe Ser Val Gly Gln His Asn Tyr Glu Arg Gly Pro Ile Gln
     385                 390                 395                 400

Trp Met Ala Cys Glu Asn Lys Gly Tyr Tyr Tyr Glu Ile Pro Ser Ile
                    405                 410                 415

Gly Ala Ile Arg Ile Asn Thr Gln Glu Tyr Leu Asp Val Leu Gly Arg
                    420                 425                 430

Pro Met Val Leu Ala Gly Asp Lys Ala Lys Gln Val Gln Trp Thr Asn
                    435                 440                 445

Val Tyr Leu Asp Ala Leu Glu Leu Gly Leu Val Ile Thr Gly Thr Leu
     450                 455                 460

Pro Val Phe Asn Ile Thr Gly Gln Phe Glu Asn Lys Thr Asn Leu Lys
     465                 470                 475                 480

Asn Gln Leu Ile Leu Gly Val Met Gly Val Asp Val Ser Leu Glu Asp
                    485                 490                 495
```

```
Ile Lys Arg Leu Thr Pro Arg Phe Thr Leu Cys Pro Asn Gly Tyr Tyr
            500                 505                 510

Phe Ala Ile Asp Pro Asn Gly Tyr Ala Leu Leu His Pro Asn Leu Gln
        515                 520                 525

Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
    610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Ala Asp
        675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
    770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
            900                 905                 910
```

```
Ala Asp Ile Leu Gln Ile Gly Trp Trp Ala Thr Ala Ala Ala Trp Ser
            915                 920                 925

Ile Leu Gln Gln Phe Leu Leu Ser Leu Thr Phe Pro Arg Leu Leu Glu
        930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
        995                 1000                1005

Lys Gly Thr Cys Pro Cys Asp Thr Arg Leu Leu Ile Gln Ala Glu Gln
   1010                 1015                1020

Thr Ser Asp Gly Pro Asn Pro Cys Asp Met Val Lys Gln Pro Arg Tyr
1025                1030                1035                1040

Arg Lys Gly Pro Asp Val Cys Phe Asp Asn Asn Val Leu Glu Asp Tyr
                1045                1050                1055

Thr Asp Cys Gly Gly Val Ser Gly Leu Asn Pro Ser Leu Trp Tyr Ile
            1060                1065                1070

Ile Gly Ile Gln Phe Leu Leu Leu Trp Leu Val Ser Gly Ser Thr His
        1075                1080                1085

Arg Leu Leu
   1090

(2) INFORMATION FOR SEQ ID NO:5:

(i) SEQUENCE CHARACTERISTICS:
        (A) LENGTH: 1476 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 8..1459

(xi) SEQUENCE DESCRIPTION: SEQ ID NO:5:

CTCCCCC ATG TAT GAC GAC TCC TAC GTG CCC GGG TTT GAG GAC TCG GAG         49
        Met Tyr Asp Asp Ser Tyr Val Pro Gly Phe Glu Asp Ser Glu
            1095                1100                1105

GCG GGT TCA GCC GAC TCC TAC ACC AGC CGC CCA TCT CTG GAC TCA GAC         97
Ala Gly Ser Ala Asp Ser Tyr Thr Ser Arg Pro Ser Leu Asp Ser Asp
                1110                1115                1120

GTC TCC CTG GAG GAG GAC CGG GAG AGT GCC CGG CGT GAA GTA GAG AGC        145
Val Ser Leu Glu Glu Asp Arg Glu Ser Ala Arg Arg Glu Val Glu Ser
            1125                1130                1135

CAG GCT CAG CAG CAG CTC GAA AGG GCC AAG CAC AAA CCT GTG GCA TTT        193
Gln Ala Gln Gln Gln Leu Glu Arg Ala Lys His Lys Pro Val Ala Phe
        1140                1145                1150

GCG GTG AGG ACC AAT GTC AGC TAC TGT GGC GTA CTG GAT GAG GAG TGC        241
Ala Val Arg Thr Asn Val Ser Tyr Cys Gly Val Leu Asp Glu Glu Cys
   1155                1160                1165

CCA GTC CAG GGC TCT GGA GTC AAC TTT GAG GCC AAA GAT TTT CTG CAC        289
Pro Val Gln Gly Ser Gly Val Asn Phe Glu Ala Lys Asp Phe Leu His
1170                1175                1180                1185

ATT AAA GAG AAG TAC AGC AAT GAC TGG TGG ATC GGG CGG CTA GTG AAA        337
Ile Lys Glu Lys Tyr Ser Asn Asp Trp Trp Ile Gly Arg Leu Val Lys
```

```
            1190               1195                1200
GAG GGC GGG GAC ATC GCC TTC ATC CCC AGC CCC CAG CGC CTG GAG AGC     385
Glu Gly Gly Asp Ile Ala Phe Ile Pro Ser Pro Gln Arg Leu Glu Ser
            1205               1210                1215

ATC CGG CTC AAA CAG GAG CAG AAG GCC AGG AGA TCT GGG AAC CCT TCC     433
Ile Arg Leu Lys Gln Glu Gln Lys Ala Arg Arg Ser Gly Asn Pro Ser
            1220               1225                1230

AGC CTG AGT GAC ATT GGC AAC CGA CGC TCC CCT CCG CCA TCT CTA GCC     481
Ser Leu Ser Asp Ile Gly Asn Arg Arg Ser Pro Pro Pro Ser Leu Ala
            1235               1240                1245

AAG CAG AAG CAA AAG CAG GCG GAA CAT GTT CCC CCA TAT GAC GTG GTG     529
Lys Gln Lys Gln Lys Gln Ala Glu His Val Pro Pro Tyr Asp Val Val
1250                1255                1260                1265

CCC TCC ATG CGG CCT GTG GTG CTG GTG GGA CCC TCT CTG AAA GGT TAT     577
Pro Ser Met Arg Pro Val Val Leu Val Gly Pro Ser Leu Lys Gly Tyr
            1270               1275                1280

GAG GTC ACA GAC ATG ATG CAG AAG GCT CTC TTC GAC TTC CTC AAA CAC     625
Glu Val Thr Asp Met Met Gln Lys Ala Leu Phe Asp Phe Leu Lys His
            1285               1290                1295

AGA TTT GAT GGC AGG ATC TCC ATC ACC CGA GTC ACA GCC GAC CTC TCC     673
Arg Phe Asp Gly Arg Ile Ser Ile Thr Arg Val Thr Ala Asp Leu Ser
            1300               1305                1310

CTG GCA AAG CGA TCT GTG CTC AAC AAT CCG GGC AAG AGG ACC ATC ATT     721
Leu Ala Lys Arg Ser Val Leu Asn Asn Pro Gly Lys Arg Thr Ile Ile
            1315               1320                1325

GAG CGC TCC TCT GCC CGC TCC AGC ATT GCG GAA GTG CAG AGT GAG ATC     769
Glu Arg Ser Ser Ala Arg Ser Ser Ile Ala Glu Val Gln Ser Glu Ile
1330                1335                1340                1345

GAG CGC ATA TTT GAG CTG GCC AAA TCC CTG CAG CTA GTA GTG TTG GAC     817
Glu Arg Ile Phe Glu Leu Ala Lys Ser Leu Gln Leu Val Val Leu Asp
            1350               1355                1360

GCT GAC ACC ATC AAC CAC CCA GCA CAG CTG GCC AAG ACC TCG CTG GCC     865
Ala Asp Thr Ile Asn His Pro Ala Gln Leu Ala Lys Thr Ser Leu Ala
            1365               1370                1375

CCC ATC ATC GTC TTT GTC AAA GTG TCC TCA CCA AAG GTA CTC CAG CGT     913
Pro Ile Ile Val Phe Val Lys Val Ser Ser Pro Lys Val Leu Gln Arg
            1380               1385                1390

CTC ATT CGC TCC CGG GGG AAG TCA CAG ATG AAG CAC CTG ACC GTA CAG     961
Leu Ile Arg Ser Arg Gly Lys Ser Gln Met Lys His Leu Thr Val Gln
            1395               1400                1405

ATG ATG GCA TAT GAT AAG CTG GTT CAG TGC CCA CCG GAG TCA TTT GAT    1009
Met Met Ala Tyr Asp Lys Leu Val Gln Cys Pro Pro Glu Ser Phe Asp
1410                1415                1420                1425

GTG ATT CTG GAT GAG AAC CAG CTG GAG GAT GCC TGT GAG CAC CTG GCT    1057
Val Ile Leu Asp Glu Asn Gln Leu Glu Asp Ala Cys Glu His Leu Ala
            1430               1435                1440

GAG TAC CTG GAG GTT TAC TGG CGG GCC ACG CAC CCA GCC CCT GGC        1105
Glu Tyr Leu Glu Val Tyr Trp Arg Ala Thr His His Pro Ala Pro Gly
            1445               1450                1455

CCC GGA CTT CTG GGT CCT CCC AGT GCC ATC CCC GGA CTT CAG AAC CAG    1153
Pro Gly Leu Leu Gly Pro Pro Ser Ala Ile Pro Gly Leu Gln Asn Gln
            1460               1465                1470

CAG CTG CTG GGG GAG CGT GGC GAG GAG CAC TCC CCC CTT GAG CGG GAC    1201
Gln Leu Leu Gly Glu Arg Gly Glu Glu His Ser Pro Leu Glu Arg Asp
            1475               1480                1485

AGC TTG ATG CCC TCT GAT GAG GCC AGC GAG AGC TCC CGC CAA GCC TGG    1249
Ser Leu Met Pro Ser Asp Glu Ala Ser Glu Ser Ser Arg Gln Ala Trp
1490                1495                1500                1505

ACA GGA TCT TCA CAG CGT AGC TCC CGC CAC CTG GAG GAG GAC TAT GCA    1297
```

```
Thr Gly Ser Ser Gln Arg Ser Ser Arg His Leu Glu Glu Asp Tyr Ala
                    1510                1515                1520

GAT GCC TAC CAG GAC CTG TAC CAG CCT CAC CGC CAA CAC ACC TCG GGG      1345
Asp Ala Tyr Gln Asp Leu Tyr Gln Pro His Arg Gln His Thr Ser Gly
            1525                1530                1535

CTG CCT AGT GCT AAC GGG CAT GAC CCC CAA GAC CGG CTT CTA GCC CAG      1393
Leu Pro Ser Ala Asn Gly His Asp Pro Gln Asp Arg Leu Leu Ala Gln
        1540                1545                1550

GAC TCA GAA CAC AAC CAC AGT GAC CGG AAC TGG CAG CGC AAC CGG CCT      1441
Asp Ser Glu His Asn His Ser Asp Arg Asn Trp Gln Arg Asn Arg Pro
    1555                1560                1565

TGG CCC AAG GAT AGC TAC TGACAGCCTC CTGCTGC                           1476
Trp Pro Lys Asp Ser Tyr
1570                1575

(2) INFORMATION FOR SEQ ID NO:6:

(i) SEQUENCE CHARACTERISTICS:
          (A) LENGTH: 484 amino acids
          (B) TYPE: amino acid
          (D) TOPOLOGY: linear (ii) MOLECULE TYPE: protein (xi) SEQUENCE DESCRIPTION: SEQ ID NO:6:

Met Tyr Asp Asp Ser Tyr Val Pro Gly Phe Glu Asp Ser Glu Ala Gly
 1               5                  10                  15

Ser Ala Asp Ser Tyr Thr Ser Arg Pro Ser Leu Asp Ser Asp Val Ser
            20                  25                  30

Leu Glu Glu Asp Arg Glu Ser Ala Arg Arg Glu Val Glu Ser Gln Ala
        35                  40                  45

Gln Gln Gln Leu Glu Arg Ala Lys His Lys Pro Val Ala Phe Ala Val
    50                  55                  60

Arg Thr Asn Val Ser Tyr Cys Gly Val Leu Asp Glu Glu Cys Pro Val
65                  70                  75                  80

Gln Gly Ser Gly Val Asn Phe Glu Ala Lys Asp Phe Leu His Ile Lys
                85                  90                  95

Glu Lys Tyr Ser Asn Asp Trp Trp Ile Gly Arg Leu Val Lys Glu Gly
            100                 105                 110

Gly Asp Ile Ala Phe Ile Pro Ser Pro Gln Arg Leu Glu Ser Ile Arg
        115                 120                 125

Leu Lys Gln Glu Gln Lys Ala Arg Arg Ser Gly Asn Pro Ser Ser Leu
    130                 135                 140

Ser Asp Ile Gly Asn Arg Arg Ser Pro Pro Ser Leu Ala Lys Gln
145                 150                 155                 160

Lys Gln Lys Gln Ala Glu His Val Pro Pro Tyr Asp Val Val Pro Ser
                165                 170                 175

Met Arg Pro Val Val Leu Val Gly Pro Ser Leu Lys Gly Tyr Glu Val
            180                 185                 190

Thr Asp Met Met Gln Lys Ala Leu Phe Asp Phe Leu Lys His Arg Phe
        195                 200                 205

Asp Gly Arg Ile Ser Ile Thr Arg Val Thr Ala Asp Leu Ser Leu Ala
    210                 215                 220

Lys Arg Ser Val Leu Asn Asn Pro Gly Lys Arg Thr Ile Ile Glu Arg
225                 230                 235                 240

Ser Ser Ala Arg Ser Ser Ile Ala Glu Val Gln Ser Glu Ile Glu Arg
                245                 250                 255
```

-continued

```
Ile Phe Glu Leu Ala Lys Ser Leu Gln Leu Val Val Leu Asp Ala Asp
            260                 265                 270

Thr Ile Asn His Pro Ala Gln Leu Ala Lys Thr Ser Leu Ala Pro Ile
            275                 280                 285

Ile Val Phe Val Lys Val Ser Ser Pro Lys Val Leu Gln Arg Leu Ile
    290                 295                 300

Arg Ser Arg Gly Lys Ser Gln Met Lys His Leu Thr Val Gln Met Met
305                 310                 315                 320

Ala Tyr Asp Lys Leu Val Gln Cys Pro Pro Glu Ser Phe Asp Val Ile
                325                 330                 335

Leu Asp Glu Asn Gln Leu Glu Asp Ala Cys Glu His Leu Ala Glu Tyr
                340                 345                 350

Leu Glu Val Tyr Trp Arg Ala Thr His His Pro Ala Pro Gly Pro Gly
            355                 360                 365

Leu Leu Gly Pro Pro Ser Ala Ile Pro Gly Leu Gln Asn Gln Gln Leu
        370                 375                 380

Leu Gly Glu Arg Gly Glu His Ser Pro Leu Glu Arg Asp Ser Leu
385                 390                 395                 400

Met Pro Ser Asp Glu Ala Ser Glu Ser Ser Arg Gln Ala Trp Thr Gly
                405                 410                 415

Ser Ser Gln Arg Ser Ser Arg His Leu Glu Glu Asp Tyr Ala Asp Ala
                420                 425                 430

Tyr Gln Asp Leu Tyr Gln Pro His Arg Gln His Thr Ser Gly Leu Pro
            435                 440                 445

Ser Ala Asn Gly His Asp Pro Gln Asp Arg Leu Leu Ala Gln Asp Ser
        450                 455                 460

Glu His Asn His Ser Asp Arg Asn Trp Gln Arg Asn Arg Pro Trp Pro
465                 470                 475                 480

Lys Asp Ser Tyr
```

NUCLEIC ACID ENCODING HUMAN NEURONAL CALCIUM CHANNEL SUBUNITS

BACKGROUND OF THE INVENTION

Calcium channels are multi-subunit protein complexes that span the plasma membrane and are involved in the movement of calcium ions into the cell. Voltage-dependent calcium channels, the most common type of calcium channels, are classified as L-, T-, N-, or P-type channels, based on conductance levels, sensitivity to agonists and antagonists, and holding potential (K. Dunlap et al., *Trends Neurosci.* 18: 89–98 (1995)). Calcium channels contain two large subunits, α1 and α2, having molecular weights between about 130 and about 200 kDa, and one to three smaller subunits, such as β, and/or γ subunits, each having a molecular weight that is usually less than about 60 kDa. At least one of the large subunits is glycosylated, and a smaller subunit may be glycosylated as well. Subunit α1 is approximately 200 to about 230 kDa, based on sodium dodecylsulfate polyacrylamide gel electrophoresis (SDS-PAGE). This subunit forms the pore through which calcium enters cells. Subunit α2 is approximately 160 to 190 kDa under non-reducing conditions on SDS-PAGE. The γ subunit is about 52 to 65 kDa (SDS-PAGE); it is insensitive to reducing conditions. The γ subunit, which is not observed in nervous tissue or in other certain preparations, is a glycoprotein of approximately 30 to 33 kDa (SDS-PAGE).

Investigation of particular calcium channel subtypes is rendered difficult by the presence of a mixture of different tissue-specific types of calcium channels in cells. Study of particular subtypes is essential, however, because of the importance of intracellular calcium levels in contributing to vital cellular processes including neurotransmitter release, muscle contraction, pacemaker activity, and secretion of hormones and other substances. A need remains for identifying and studying individual calcium channel subtypes.

SUMMARY OF THE INVENTION

The current invention pertains to the isolation and sequencing of nucleic acids encoding three subunits of human N-type calcium channel: an α1B subunit, an α2δ subunit, and a β3 subunit. Previously unknown alterations are present in the sequence of nucleotides encoding each of the subunits. The nucleic acid encoding the α1B subunit has a change from G to A at position 194; a change from T to G at position 2559; a change from G to A at position 6470; and a deletion of nucleotides 4814–4819. The nucleic acid encoding the α2δ subunit has a change from A to C at position 329; a change from G to C at position 1191; a change from G to C at position 1219; a change from T to C at position 1596; a change from T to C at position 1980; a change from A to G at position 2090; and a change from A to G at position 3261. The nucleic acid encoding the β3 subunit has a change from C to G at position 46; a TCC insertion at position 119; a change from A to T at position 203; a change from C to T at position 300; a change from C to G at position 303; a change from A to G at position 420; a change from C to T at position 438; a change from T to C at position 477; a change from T to G at position 486; a change from G to A at position 534; a change from A to C at position 552; a change from G to T at position 561; an ATG insertion at position 978; a change from T to A at position 1064; a change from CG to GC at positions 1283–1284; or a change from C to T at position 1308. Certain of these changes result in amino acid alterations in the encoded proteins, while others are synonymous changes.

Vectors containing the nucleic acids encoding the subunits described above have been prepared, as have host cells containing the nucleic acids. Methods of isolating nucleic acids encoding related calcium channel subunits, by employing hybridization of the nucleic acids of the invention to nucleic acid libraries, are now available by virtue of the discoveries described herein. Also available are the subunit proteins encoded by the nucleic acids, and also fusion proteins comprising the subunit proteins. Antibodies to the subunit proteins can also be generated. Assays to identify agents that modulate calcium channel activity are described, in which test cells are exposed to the agent to be tested and a calcium channel-selective ion; depolarizing the cell membrane of the test cell; detecting current flowing into the cell; and comparing the current to that of a control cell, wherein a difference in the current detected in the test cell, as compared with the current of the control cell, indicates that the agent modulates calcium channel activity. In addition, methods of diagnosing diseases associated with particular calcium channels, such as Lambert-Eaton syndrome, are described, using assays to detect the presence of calcium channel-specific antibodies in a sample from the individual suspected of having the disease.

The changes that are present in the subunits described herein may produce functional differences in the calcium channel formed by the three subunits, which will have an effect on the interaction between the calcium channels and agonists or antagonists of the channels. Furthermore, calcium channel subunits described herein are an advantageous combination, because the β3 subunit is normally found associated with an α1B subunit in vivo; thus, this combination closely resembles the calcium channel in vivo.

BRIEF DESCRIPTION OF THE DRAWINGS

The FIGURE is a graphic representation of average counts per minute (CPM) for omega-conotoxin GVIA-sensitive potassium-stimulated calcium uptake in cells transfected with the three human calcium channel subunits.

DETAILED DESCRIPTION OF THE INVENTION

The current invention pertains to the isolation and identification of DNA encoding subunits of a particular calcium channel. As described in the Examples below, cDNA encoding an α1B subunit, an α2δ subunit, and a β3 subunit of the human N-type calcium channel has been isolated. The cDNA clones have been inserted into expression vectors, and are stably expressed in transformed cell lines. The resulting transformed cells express each of the three mRNA encoding the individual subunits of the N-type channel. The transformed cells show omega-conotoxin GVIA binding activity, and omega-conotoxin GVIA toxin sensitive potassium-stimulated calcium uptake, indicating that the proteins expressed by the clones are capable of forming a functioning calcium channel.

As a result of this discovery, nucleic acids encoding the three subunits, as well as vectors containing the nucleic acids encoding one or more of the subunits, host cells containing the nucleic acids encoding one or more of the subunits, and methods of isolating nucleic acids encoding related calcium channel subunits are now available. The subunit proteins, fusion proteins comprising the subunit proteins, and antibodies to the subunit proteins, as well as assays to identify agents that modulate calcium channel activity, are also described. Agents that modulate calcium channel activity can be used to treat certain central nervous system disorders by altering calcium channel activity. In addition, methods of diagnosing diseases associated with particular calcium channels, such as Lambert-Eaton syndrome, are described.

A "nucleic acid encoding a calcium channel subunit", as used herein, is a sequence of nucleotides which encodes either an α1B subunit, an α2δ subunit, or a β3 subunit of the N-type calcium channel. Nucleic acid encoding a calcium channel subunit can be either cDNA, DNA or mRNA. The nucleic acid encoding a calcium channel subunit is "isolated," indicating that it has been purified according to standard techniques known in the art (for example, such as by techniques described by Sambrook et al. (eds), in Molecular Cloning: A Laboratory Manual, (2nd ed.), Cold Spring Harbor Laboratory Press (1989)).

In one embodiment, nucleic acid encoding a calcium channel α1B subunit has the sequence of (SEQ ID NO. 1). In another embodiment, nucleic acid encoding a calcium channel α1B subunit is a nucleic acid encoding a functional equivalent of the subunit encoded by sequence of (SEQ ID NO. 1). A "functional equivalent" has the same function as the calcium channel subunit, but is encoded by a nucleic acid that may have minor variations in the sequence of nucleotides, in comparison to the nucleic acid encoding the subunit. A nucleic acid encoding a functional equivalent is referred to herein as an "equivalent" nucleic acid. Minor variations in equivalent nucleic acids include variations that result in no alteration of the encoded amino acid sequence (synonymous changes); variations that result in conservative amino acid substitutions in the encoded amino acid sequence; and/or minor deletions or insertions of nucleotides that do not alter the activity of the peptide. Such changes are readily known to the skilled artisan. For example, representative conservative amino acid changes include: alanine to glycine or serine; arginine to lysine; asparagine to glutamine or histidine; cysteine to serine; glutamine to asparagine; glutamate to aspartate; glycine to alanine or proline; histidine to asparagine or glutamine; isoleucine to leucine or valine; leucine to isoleucine or valine; lysine to arginine or glutamine; methionine to leucine tyrosine, or isoleucine; phenylalanine to methionine, leucine to tyrosine; serine to threonine; threonine to serine; tryptophan to tyrosine; tyrosine to tryptophan or phenylalanine; valine to isoleucine or leucine.

A functional equivalent of a subunit has an activity that is equivalent to the subunit. "Activity" refers to the ability of the peptide to form a functional calcium channel with other necessary subunits. A functional calcium channel is a calcium channel that is able to provide for and regulate entry of calcium channel-selective ions, including calcium, in response to appropriate stimuli, and/or is able to bind ligands having affinity for the calcium channel. The activity of a calcium channel may be assessed in vitro by standard methods, such as electrophysiological or other methods described below.

Nucleic acids encoding a functional equivalent of a calcium channel α1B subunit, include at least one of the following alterations, in comparison to the nucleic acid sequence in GenBank sequence data base, Accession number M94172 (see Williams, M. E. et al., *Science* 257: 389–395 (1992)): a change from G to A change at position 194; a change from T to G at position 2559; a change from G to A at position 6470; or a deletion of nucleotides 4814–4819. The nucleic acid having the sequence of SEQ ID NO. 1, as well as nucleic acids encoding a functional equivalent of the subunit encoded by the sequence of (SEQ ID No. 1), are collectively referred to herein as a nucleic acid encoding a calcium channel α1B subunit.

A nucleic acid encoding a calcium channel α2δ subunit has the sequence of SEQ ID NO. 3, or a sequence of nucleotides encoding a functional equivalent of the subunit encoded by the SEQ ID NO. 3. A nucleic acid encoding a functional equivalent of the subunit encoded by the sequence of 2 SEQ ID NO. 3 includes at least one of the following alterations, in comparison to the *GenBank sequence data base, Accession number M*76559 (Williams M. E. et al., *Neuron* 8: 71–84 (1992)): a change from A to C at position 329; a change from G to C at position 1191; a change from G to C at position 1219; a change from T to C at position 1596; a change from T to C at position 1980; a change from A to G at position 2090; or a change from A to G at position 3261.

A nucleic acid encoding a calcium channel β3 subunit has the sequence of SEQ ID NO. 5, or the sequence of nucleotides encoding a functional equivalent of the subunit encoded by SEQ ID NO. 5. A sequence of nucleotides encoding a functional equivalent of the subunit encoded by SEQ ID NO. 5 includes at least one of the following alterations, in comparison to the GenBank sequence data base, Accession number L27584 (see Collin, T. et al., *Eur. J. Biochem.* 220(1): 257–262 (1994)): a change from C to G at position 46; a TCC insertion at position 119; a change from A to T at position 203; a change from C to T at position 300; a change from C to G at position 303; a change from A to G at position 420; a change from C to T at position 438; a change from T to C at position 477; a change from T to G at position 486; a change from G to A at position 534; a change from A to C at position 552; a change from G to T at position 561; an ATG insertion at position 978; a change from T to A at position 1064; a change from CG to GC at positions 1283–1284; or a change from C to T at position 1308.

The nucleic acids encoding calcium channel subunits of the invention can be used to isolate other nucleic acids encoding related subunits. For example, all or a portion of one of the nucleic acids encoding a calcium channel subunit can be used as a probe to isolate nucleic acids from a nucleic acid library by hybridization techniques. A "portion" of the nucleic acid indicates a part of the nucleic acid that contains one of the specific alterations described above. Stringency conditions should be tailored to eliminate hybridization of the probes to extraneous nucleic acid sequences (see Sambrook et al. (eds), Molecular Cloning: A Laboratory Manual, (2nd ed.), Cold Spring Harbor Laboratory Press (1989), particularly chapter 11.45). In a preferred embodiment, stringency conditions are selected such that the nucleic acid encoding a calcium channel subunit, or a portion of the nucleic acid, selectively hybridizes to a second nucleic acid (the target nucleic acid). "Selective hybridization" indicates that the hybridization is of sufficient specificity to allow the target nucleic acid to be identified or isolated from other nucleic acids. Generally, medium stringency conditions will allow selective hybridization. Nucleic acids that encode a calcium channel subunit, and are capable of selectively hybridizing, under medium or high stringency conditions, to all or a portion of a nucleic acid encoding a calcium channel subunit of the invention, or to all or a portion of a nucleic acid encoding a functional equivalent of a calcium channel subunit of the invention, are also encompassed by the invention.

Nucleic acids encoding a calcium channel α1B subunit, a calcium channel α2δ subunit, or a calcium channel β3 subunit, as described above, can be inserted into a vector to facilitate expression. The vector is capable of expressing nucleic acids that are in operative linkage with endogenous or exogenous regulatory sequences; it may be a plasmid, a phage, a virus, or other vector. The vector can contain other elements, such as transcriptional promoter elements, enhancer elements, splicing signals, termination and polyadenylation signals, viral replicons, and/or bacterial plasmid sequences. Upon introduction of the vector into a host cell, the nucleic acid inserted into the vector is expressed. The vector can contain more than one nucleic acid encoding a calcium channel subunit of the invention. For example, a vector can contain nucleic acids encoding a calcium channel α1B subunit, as well as nucleic acids encoding a calcium channel α2δ subunit. If only one subunit is used, it is understood that other known sequences are present to encode a functional protein.

A vector containing the nucleic acids encoding a calcium channel subunit of the invention, as described above, can be transformed or transfected into an appropriate host cell for expression. Alternatively, a nucleic acid encoding a calcium channel subunit of the invention can be inserted directly into the host cell. The nucleic acids can be introduced into the cell in a manner such that they are integrated into the host cell genome; alternatively, they can be maintained episomally.

Representative host cells include *Escherichia coli*, HEK 293 cells, Chinese hamster ovary (CHO) cells, African green monkey cells, mouse L cells, amphibian oocytes, and CHODUX cells (Mitchell, P. J. et al., *Mol. Cell Biol.* 6(6)1926–35 (1986)). In a preferred embodiment, the host cell does not naturally contain nucleic acids encoding, or produce calcium channels comprising, α1B, α2δ, or β3 subunits, in order to facilitate distinguishing the nucleic acids and encoded subunits of the invention from other, native nucleic acids and subunits. In a more preferred embodiment, the host cell does not express or produce endogenous calcium channel subunits of the type, or in an amount, that substantially interferes with detection of the nucleic acids and encoded subunits of the invention.

A single α1 subunit is sufficient to form a calcium channel; therefore, at least the nucleic acid encoding the α1B subunit is introduced into the host cell. In a preferred embodiment, nucleic acids encoding each of the three subunits are introduced into the host cell such that the host cell expresses the subunits and includes one or more of them in membrane-spanning calcium channels. In a preferred embodiment, the host cell expresses functional calcium channels that are capable of controlling movement of calcium channel-selective ions and/or binding compounds. In a more preferred embodiment, the calcium channels are composed substantially or entirely of the three subunits encoded by the nucleic acids of the invention, in order to generate a calcium channel that is closer to the normal physiologic state of the channel in the mammalian central nervous system. A host cell which has been transformed or transfected as described above is also referred to herein as a transformed cell.

Host cells transformed or transfected with nucleic acids encoding one or more of the calcium channel subunits of the invention can be used for screening for compounds that modulate calcium channel activity. Because the host cells have a homogeneous population of calcium channels, they provide a means to identify agents that specifically modulate activity of the particular calcium channels. An agent that modulates (e.g., enhances or upregulates, or inhibits or downregulates) calcium channel activity is an agent that affects the ability of the calcium channel to pass calcium channel-selective ions, or affects other detectable calcium channel characteristics, such as current kinetics. The agent may affect the calcium channel directly or indirectly.

For example, transformed cells can be used in assays that identify agents that are agonists or antagonists of calcium channel activity. To identify agents that modulate calcium channel activity, a transformed cell (or a culture of transformed cells), used as a "test" cell, is maintained in a solution containing an agent to be tested for its ability to modulate calcium channel activity (the test agent) and a calcium channel selective ion. A "calcium channel selective ion" refers to an ion that is capable of flowing through, or being blocked from flowing through, a calcium channel which spans a cellular membrane under conditions which would permit or block the flow of calcium ions. $Ba^{2+}$ is an example of a calcium channel selective ion. The cell membrane of the test cell is then depolarized, and current flowing into the test cell is detected. If the current that is detected is different from the current produced by depolarizing the same cell or a control cell in the presence of the same calcium channel selective ion, but in the absence of the compound, then the agent modulates calcium channel activity. In a preferred embodiment, the test cell is maintained at a holding potential which substantially inactivates calcium channels prior to the depolarization step. If the current is higher in the presence of the agent than in the absence of the agent, then the agent is an agent that enhances calcium channel activity (a calcium channel agonist). If the current is lower in the presence of the agent than in the absence of the agent, then the agent is an agent that inhibits calcium channel activity (a calcium channel antagonist).

One "control" cell which can be used as described above, is a cell that is maintained in substantially the same manner as the test cell, with the exception that the control cell is not exposed to the agent to be tested. An alternative "control" cell is a cell which is identical to the test cell, except that it does not express functional calcium channels.

Agents identified by these methods can be used to modulate activity of calcium channels in vivo. The in vitro assays described above should accurately predict relative efficacy of an agent as an agonist or an antagonist of calcium channels, since the calcium channel subunits described herein are subtype- and tissue-specific. Specific disease targets include central nervous system disorders, including stroke, cerebral ischemia, epilepsy, chronic pain, head trauma, and other central nervous system diseases or conditions in which too much or too little neurotransmitter is released. The agent is administered by an appropriate route, such as orally, subcutaneously, transdermally, intravenously, intramuscularly, intraperitoneally, topically, rectally, vaginally, nasally, or via an implanted reservoir. The agent can be administered in dosage formulations containing conventional, non-toxic, physiologically-acceptable carriers, adjuvants, and/or vehicles. The formulation in which the agent is administered will depend at least in part on the route by which it is administered. The agent is administered in an effective amount, which is that amount necessary to alleviate, reduce, eliminate, or prevent the symptoms associated with the disease, disorder or condition to be treated. More than one agent can be administered; if more than agent is used, the effective amount is that amount of the combination of agents that is necessary to alleviate, reduce, eliminate or prevent the symptoms associated with disease, disorder or condition. The effective amount will be determined on an individual basis, and will be based in part, on consideration of the particular agent, the individual's size and gender, the severity of the symptoms to be treated, the result sought, and the disease, disorder or condition to be treated. The effective amount can be administered in a series of doses separated by appropriate intervals, such as hours, days, or weeks. Alternatively, the effective amount can be administered as a sustained release dose, such as by a controlled-release dosage formulation.

Purified proteins encoded by a nucleic acid encoding a calcium channel α1B subunit, a calcium channel α2δ subunit, or a calcium channel β3 subunit, as described above, are also described. The proteins (also referred to herein as calcium channel subunits of the invention) can be isolated from a host cell transfected or transformed with the nucleic acid encoding the subunit. Representative proteins include a calcium channel α1B subunit having the amino acid sequence 7 SEQ ID NO. 2; a calcium channel α2δ subunit having the amino acid sequence 7 SEQ ID NO. 4; or a calcium channel β3 subunit having the amino acid sequence of 7 SEQ ID NO. 6.

Fusion proteins comprising the calcium channel α1B subunit, a calcium channel α2δ subunit, or a calcium channel β3 subunit can also be generated using standard techniques. For example, a fusion nucleic acid can be generated by splicing, or attaching the nucleic acid encoding the calcium channel subunit to a nucleic acid encoding another protein or peptide (the fusion partner or protein), or by inserting the nucleic acid encoding the calcium channel subunit and the fusion protein into a common vector; the fusion nucleic acid can then be transformed, transfected, or inserted into a host cell for transcription and translation.

Antibodies (or immunoglobulins) to the calcium channel subunits of the invention can be generated. The term "antibody", as used herein, encompasses both polyclonal and monoclonal antibodies, as well as mixtures of more than one antibody reactive with a calcium channel subunit of the invention (e.g., a cocktail of different types of monoclonal antibodies reactive with the mutant protein or protein fragment). The term antibody is further intended to encompass whole antibodies and/or biologically functional fragments thereof, chimeric antibodies comprising portions from more than one species, humanized antibodies, human-like antibodies, and bifunctional antibodies. Biologically functional antibody fragments which can be used are those fragments sufficient for binding of the antibody fragment to the calcium channel subunit of interest. Once the antibodies are raised, they are assessed for the ability to bind to the calcium channel subunit of interest. Conventional methods can be used to perform this assessment. Antibodies can also be raised to calcium channels formed by the combination of the calcium channel α1B subunit, the calcium channel α2δ subunit, and the calcium channel β3 subunit described herein.

The chimeric antibodies can comprise portions derived from two different species (e.g., a constant region from one species and variable or binding regions from another species). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

Monoclonal antibodies (mAb) reactive with a calcium channel subunit of the invention, or a calcium channel formed by the subunits, can be produced using somatic cell hybridization techniques (Kohler and Milstein, *Nature* 256: 495–497 (1975)) or other techniques. In a typical hybridization procedure, purified calcium channel subunit, or calcium channels, can be used as the immunogen. An animal is immunized with the immunogen to obtain antibody-producing spleen cells. The species of animal immunized will vary depending on the specificity of mAb desired. The antibody producing cell is fused with an immortalizing cell (e.g., a myeloma cell) to create a hybridoma capable of secreting antibodies. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal in a similar fashion as described above for the production of monoclonal antibodies. The animal is maintained under conditions whereby antibodies reactive with the calcium channel subunit of interest, or the calcium channel, are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

Antibodies that are specific for the calcium channel subunits of the invention, or for the calcium channel formed by the three subunits of the invention, can be used for immunohistochemistry to monitor distribution and expression density of the various subunits, or of the calcium channels themselves, in different tissues, including in normal and in diseased tissue. The antibodies can also be used as a therapeutic agent, in order to modulate calcium channel activity, as described in detail above.

Antibodies that are specific for the calcium channel subunits of the invention, or for the calcium channel formed by the three subunits of the invention, can also be used to facilitate diagnosis of Lambert-Eaton Syndrome (LES). LES autoimmune disease is characterized by insufficient release of acetylcholine from motor nerve terminals which normally are responsive to nerve impulses. IgG from LES patients block individual voltage-dependent calcium channels and thus inhibit calcium channel activity (Kim and Neher, *Science* 239: 405–8 (1988)). To diagnose LES, a test sample of blood or other bodily fluid is obtained from an individual suspected of having or carrying the disease. The test sample is contacted with a calcium channel subunit of the invention, or a calcium channel formed by the three subunits of the invention, under conditions which would allow any antibody which is specific for the calcium channel subunit or the calcium channel, and which may be present in the test sample, to bind. Binding of antibody to the calcium channel subunit of the invention, or the calcium channel formed by the subunits of the invention, if such binding exists, is then detected. The presence of binding indicates that the individual has antibodies to the calcium channel, and thus, is afflicted with LES.

The invention is further illustrated by the following Examples.

EXAMPLE 1

Isolation and Expression of Clones for Human α1B Subunit of N-Type Channel

Sequences referred to herein are described in comparison to the sequence encoding an α1B subchannel, described in the GenBank sequence data base, Accession number M94172 (see William, M. E. et al., *Science* 257: 389–395 (1992)).

A. Isolation of Primary Clones

Three primary clones, each containing a portion of the $\alpha_{1B}$ subunit, were obtained by hybridization under low stringency conditions with human cerebellum library at 50° C. in 6× sodium chloride, sodium citrate (SCC) overnight. Hybridized nucleic acids were washed using standard techniques (see Sambrook et al. (eds), Molecular Cloning: A Laboratory Manual, (2nd ed.), Cold Spring Harbor Laboratory Press (1989)).

First, clone pN, which spans sequences 54–1405, was cloned into the SmaI site of pSK-(Bluescript). The SacI site of the polylinker is at the 5' end. The SmaI site was destroyed. pN has a single nucleotide change (G to A at position 194), which alters the amino acid at the corresponding position in the protein from gly to ser.

The second clone, pM, spans sequences 978–4562. EcoRI/blunt fragment was inserted into EcoRI/SmaI sites of pSK-. The KpnI site of the polylinker was at the 5' end. The SmaI site was destroyed. pM has a single nucleotide change (T to G at position 2559), which results in an alteration of the amino acid at the corresponding position from leu to arg.

Clone pC, which spans sequences 4105–7322, was also isolated. An EcoRI/XbaI fragment was cloned into EcoRI/XbaI restricted pNK-CMV vector. The SacI site of the polylinker is at the 5' end. Clone pC has two changes: a single nucleotide change at position 6470 (G to A), resulting in an alteration of the corresponding amino acid from gly to ser; and a six base pair deletion at nucleic acid positions 4814–4819, resulting in a deletion of the two corresponding amino acids (glu and thr).

B. Generation of pSK-Hα1

In order to generate a clone containing the entire α1B cDNA, combination vectors were made. First, pMC was created. To allow cleavage by MamI, both pM and pC were transformed into SCS110 cells (Stratagene; dam-, dcm-), and the unmethylated DNA was isolated. pC was digested with XbaI and MamI, and the 2930 bp fragment was isolated. pM was also digested with MamI and XbaI, and the 6.4 kb vector+ insert band was isolated. These two fragments were ligated together to create pMC. The fusion point is the MamI site at position 4395.

pNMC, a fusion of pN and pMC, was then generated. pN was restricted with KpnI and XbaI, and the 1.4 kb insert was isolated. pMC was restricted with XbaI and partially restricted with KpnI. The 6012 XbaI/KpnI fragment was isolated. These two fragments were ligated together, and the ligation reaction was then cut with XbaI. The resulting fragments were then ligated to a pSK- vector restricted with XbaI. The resulting plasmid contains the entire coding sequence of α1, with 91 bp 5' UT, and 157 bp 3' UT (pos 54–7322). the fusion point is the KpnI site at position 1310. The KpnI site of the pSK- polylinker is at the 5' end. This pNMC vector is referred to as pSK-Hα1.

C. Expression Clones

Two expression clones were generated. The first, pNK-Hα1, was constructed by isolating the XbaI insert of pSK-Hα1; this XbaI insert was inserted into the XbaI site of pNK-CMV. The polylinker SacI site is at the 5' end.

A second expression clone, pNK-Hα1-Koz, was also generated. A 540 primer containing an optimized Kozak sequence (CCACC<u>ATG</u>G) (SEQ ID No. 7), an EcoRI site, and surrounding bases was synthesized. A 3' primer spanning the BglII site at position 1463 was also synthesized. These primers were used to PCR the α1 5' end from pNK-Hα1. This product was cut with EcoRI and BglII, and cloned into a likewise restricted pNK-Hα1 plasmid. The resulting truncated plasmid contains the Kozak sequence and has been shown to express at least as well as the parent plasmid in transient transfection studies.

The Hα1 gene thus includes several changes from the previously known sequence presented in the GenBank sequence data base, Accession number M94172. A single nucleotide change (G to A at position 194), alters the amino acid at the corresponding position in the protein from gly to ser; a single nucleotide change (T to G at position 2559), results in an alteration of the amino acid at the corresponding position from leu to arg. Also, a single nucleotide change at position 6470 (G to A), results in an alteration of the corresponding amino acid from gly to ser; and a six base pair deletion at nucleic acid positions 4814–4819, results in a deletion of the two corresponding amino acids (glu and thr). These alterations are summarized in Table I.

TABLE I

α1B Alterations

| Position | Nucleotide Change | Amino Acid Change |
|---|---|---|
| 194 | G to A | Gly to Ser |
| 2559 | T to G | Leu to Arg |
| 6470 | G to A | Gly to Ser |
| 4814–4819 | Deletion 6 bp | Deletion Glu and Thr |

EXAMPLE 2

Isolation and Expression of Clones for Human α2δ Subunit of N-Type Channel

Sequences referred to herein are described in comparison to the sequence encoding an α2δ subchannel, described in the GenBank sequence data base, Accssion number M76556 (Williams, M. E. et al., Neuron 8: 71–84 (1992)).

A. Isolation of Primary Clones and Generation of clone pNK-Hα2

The clone pNK-Hα2, was constructed as a fusion of two PCR clones. The template was human cerebellum Quick-Clone (Clonetech) cDNA, and the two PCR clones included sequences from 16–1409 (p2110) and from 1379–3313 (p2223). They were isolated as T/A clones in PCRII (Invitrogen) with the polylinker NotI site at the 5' end of each clone. p2110 was restricted with EcoRI and NsiI, and p2223 was restricted with NsiI and KpnI. The gel-purified inserts were fused at the NsiI site (Pos. 1394) and cloned into an EcoRI/KpnI restricted pNK-CMV vector. The SacI site is at the 5' end.

This clone, pNK-Hα2, contained certain alterations from a previously identified α2 sequence described in the GenBank sequence data base Accession number M76559 EMBL file. These alterations are summarized in Table II.

TABLE II

Alterations in Hα2δ

| Position | Nucleotide Change | Amino Acid Change |
|---|---|---|
| 329 | A to C | Ser to Arg |
| 1191 | G to C | Arg to Thr |
| 1219 | G to C | Glu to Asp |
| 1596 | T to C | Val to Ala |
| 1980 | T to C | Ile to Thr |
| 2090 | A to G | Asn to Asp |
| 3261 | A to G | Val to Ala |

B. Expression Clones

Two expression clones were generated. First, pNK-Hα2 was cut with KpnI and blunt ended. EcoRI linkers were attached. The reaction was treated with EcoRI, and the 3.3 kb EcoRI insert was isolated. This EcoRI insert was ligated into two different vectors, pED, and pBabe-CMV, which had been restricted with EcoRI. The correct orientations were selected. The resultant expression clones are referred to herein as pBabe-Hα2 and pED-Hα2.

EXAMPLE 3

Isolation and Expression of Clones for Human $\beta_3$ Subunit of N-Type Channel Sequences referred to herein are described in comparison to the sequence encoding an β3 subchannel, described in the GenBank sequence data base, Accession number L27584 (see Collin, T. et al., *Eur. J. Biochem.* 220(1): 257–262 (1994)).

A. Isolation of Primary Clones and Generation of Clone pNK-Hβ3

A blunt ended PCR product spanning sequences 21–1490 was cloned into the EcoRI site of pSK-. The template was human cerebellum QuickClone (Clonetech) cDNA, generating pSK-Hβ3. The EcoRI/KpnI insert of pSK-Hβ3 was isolated and subsequently subcloned into the EcoRI/KpnI sites of pNK-CMV. The SacI site of the polylinker is at the 5' end. This clone, pNK-Hβ3, contained certain alterations from a previously identified β3 sequence described in the HUMCALBA Genbank file. These alterations are summarized in Table III.

TABLE III

Alterations in Hβ3

| Position | Nucleotide Change | Amino Acid Change |
|---|---|---|
| 46 | C to G | Leu to Val |
| 119 | TCC insertion | Ser insertion |
| 203 | A to T | Glu to Val |
| 300 | C to T | no change |
| 303 | C to G | no change |
| 420 | A to G | no change |
| 438 | C to T | no change |
| 477 | T to C | no change |
| 486 | T to G | no change |
| 534 | G to A | no change |
| 552 | A to C | no change |
| 561 | G to T | no change |
| 978 | ATG insertion | Met insertion |
| 1064 | T to A | Leu to His |
| 1283-4 | CG to GC | Thr to Ser |
| 1308 | C to T | no change |

EXAMPLE 4

Demonstration of Formation of Calcium Channels

CHODUX cells (Mitchell, P. J. et al., *Mol. Cell Bio.* 6(6): 1926–35 (1986), Genbank M13476, M13477) were seeded on 100 mm dishes with 1 to 2×10⁶ cells, at 24 hours before transfection. Cells were transformed with each of the following three expression clones: pNK-Hα1, pNK-Hα2, and pNK-Hβ3, using CaPO$_4$ transfection kit (Stratagene Mammalian Transfection Kit) according to the manufacturer's instructions. Cells were then washed using a single PBS wash, being careful not to dislodge cells. Thirty to 35 μg DNA was used per plate, in an approximately 2:1:1 subunit ratio (20 μg α1B, 7.5 μg α2δ, 5 μg β3). Transfection was allowed to proceed for approximately 16 hours overnight.

Saturating binding experiments were performed on the cells using a protocol as described by Harpold et al. (*Science* 257: 389–395 (1992)). Briefly, reaction tubes containing ¹²⁵I-omega-conotoxin GVIA (NEN) were prepared. The ¹²⁵I-omega-conotoxin GVIA is packaged in vials of 10 μCi at a specific activity of 2200 Ci/mmol. The vial is resuspended in 450 μl water, to obtain 10 nM. For a 200 pM (saturating) final concentration, 10μl/0.5 ml reaction was used. Cells were washed 1× with PBS and resuspended with 1–2 ml binding buffer and BSA per plate by pipetting. Approximately 500,000 cells (50–100 μl) per 0.5 ml reaction were used to initiate binding reaction. The reaction was allowed to proceed for 30–60 minutes at 37° C. Subsequently, 1 ml cold wash buffer+BSA was added, and cells were pelleted by 5 minutes at 2.8 krpm at 4° C. (Sorvall RT6000). Cells were washed 1× with 2 ml cold wash buffer+BSA and resuspended by gently vortexing; subsequently, they were repelleted. After aspiration of liquid, scintillation counting was performed.

Results of the experiments demonstrated specific omega-conotoxin GVIA binding to whole cells. Specific binding indicates that the expression clones were expressed, and that the expressed subunits formed calcium channels.

EXAMPLE 5

Demonstration of Inhibition of omega-Conotoxin GVIA-Sensitive Potassium-Stimulated Calcium Uptake The uptake of $^{45}$Ca into cells was performed by an adaptation of the method of Tan, K. and A. H. Tashjian (*J. Biol. Chem.* 259: 418–426 (1984). The principle of the method involves activating ion permeation through synaptosomal calcium channels by high potassium-induced depolarization of the synaptosomal preparation. The uptake of $^{45}$Ca measured by this procedure is mediated by N-type calcium channels, and is sensitive to dihydropyridine, phenylalkylamine, and benzothiazipine Ca antagonists at therapeutically relevant concentrations (Tan and Tashjian, ibid.)

Cells were transfected with the three human calcium channel subunits described herein. Transfected cells were suspended in 15 ml growth medium (Ham's F-10 medium plus 15% heat-inactivated horse serum and 2.5% heat-inactivated fetal bovine serum). The cells were centrifuged, resuspended, and then added to T-75 flasks containing 12–15 mls growth medium, and incubated at 37° C. for approximately one week. The cells were then removed from the flask after dissociation from the walls of the flask by treatment for 5 minutes at 37° C. with 10 μM EDTA in phosphate buffered saline. The buffer was decanted, and the cells were resuspended in approximately 200 ml of growth medium. The cells were then aliquoted 200 μg/well) into each well of several 96-well plates, and grown under the aforementioned conditions for 3–4 weeks, with replacement of growth medium occurring twice per week. Cells were fed growth medium 24 hours before they are employed for $^{45}$Ca uptake determinations.

At the time of the assay, media was aspirated from each 96-well plate using a manifold designed to allow 50 μL of liquid to remain in each well. Each plate was washed and aspirated twice with a low K+ buffer solution "LKHBBS" (in mM: 5 KCl, 145 NaCl, 10 Hepes, 1 MgCl$_2$, 0.5 CaCl$_2$, 10 glucose, pH 7.4), 200 μl/well. Each plate was incubated for 10 minutes at 37° C., and aspirated as above. To each well of each plate, 50 μl of LKHBBS containing the agent in twice the final concentration was added. The agents added are set forth in Table IV.

TABLE IV

Agents Added to Transfected Cells, Demonstrating omega-Conotoxin GVIA-Sensitive Potassium-Stimulated Calcium Uptake

| Sample | Cell Type | Agent Added |
|---|---|---|
| 1 | HEK293 | Control (no agent) |
| 2 | HEK293 | 75 mM KCl |
| 3 | T9 | Control (no agent) |
| 4 | T9 | 74 mM KCl |
| 5 | T9 | SNX-111 (10 μM) |
| 6 | T9 | SNX-111 (10 μM) plus KCl (negative control) |
| 7 | T9 | gadolinium (10 μM) |
| 8 | T9 | gadolinium (10 μM) plus KCl (negative control) |

The plates were incubated for 10 minutes at room temperature. To each well of each plate, 50 μl of either of two solutions were added: (a) LKHBBS containing 1 μCi of carrier-free $^{45}$Ca, or (b) HKHBBS (a high K+ buffer containing 150 mM KCl and no NaCl, but otherwise identical to LKHBBS).

Each plate was then incubated for 5 minutes at room temperature, aspirated as above, and quenched with 200 μl/well of Quench Buffer (Ca-free LKHBBS containing 10 mM Tris-EGTA). Each plate was aspirated and rinsed with Quench Buffer a second time, then carefully aspirated to dryness. To each well of each plate 100 μl of High Safe II scintillation fluid (MicroScint (Packard)) was added. The plates were sealed, shaken, and subjected to scintillation spectrophotometry on a Microbeta 96-well Scintillation Counter (Wallac, Gaithersburg, Md., USA). Average counts per minute (CPM) are plotted in the FIGURE (numbering of data points corresponds to the numbering of agents in Table IV). Results indicated that omega-conotoxin GVIA-sensitive potassium-stimulated calcium uptake occurred in the transfected cells, and was inhibited by the agents known to inhibit L-type calcium channels, thereby demonstrating that the three subunits formed a functioning calcium channel.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

---

What is claimed is:

1. An isolated nucleic acid encoding a calcium channel α1B subunit comprising SEQ ID NO. 1.

2. The isolated nucleic acid of claim 1, wherein the nucleic acid is isolatable from human cerebellum tissue.

3. A vector comprising the isolated nucleic acid of claim 1.

4. A host cell comprising the vector of claim 3.

5. An isolated nucleic acid encoding a calcium channel α2δ subunit, comprising SEQ ID NO. 3, wherein the nucleic acid has at least one of the following alterations: AGC→CGC, resulting in ser$^{99}$→arg$^{99}$; AGG→ACG, resulting in arg$^{386}$→thr$^{386}$; GAG→CAG, resulting in glu$^{395}$→asp$^{395}$; ATA→ACA, resulting in ile$^{649}$→thr$^{649}$; AAC→GAC resulting in asn$^{686}$→asp$^{686}$ and CAG→CGG, resulting in gln$^{1076}$→arg$^{1076}$.

6. The isolated nucleic acid of claim 5, wherein the nucleic acid is isolatable from human cerebellum tissue.

7. A vector comprising the isolated nucleic acid of claim 5.

8. A host cell comprising the vector of claim 7.

9. An isolated nucleic acid encoding a calcium channel β3 subunit, comprising SEQ ID NO: 5 wherein the nucleic acid has the following alteration: GAG→GTG, resulting in glu$^{34}$→val$^{34}$.

10. The isolated nucleic acid of claim 9, wherein the nucleic acid is isolatable from human cerebellum issue.

11. A vector comprising the isolated nucleic acid of claim 9.

12. A host cell comprising the vector of claim 11.

* * * * *

UNITED STATES PATENT AND TRADEMARK OFFICE
CERTIFICATE OF CORRECTION

| | |
|---|---|
| PATENT NO. | : 6,040,436 |
| APPLICATION NO. | : 08/713118 |
| DATED | : March 21, 2000 |
| INVENTOR(S) | : Rodrigo Franco, Ai Ru Sun Chen and David Joseph Shuey |

Page 1 of 1

It is certified that error appears in the above-identified patent and that said Letters Patent is hereby corrected as shown below:

<u>Column 59, Claim 5</u>
Line 52, delete both occurrences of "99" and add therefore --2436--;
Line 53, delete both occurrences of "386" and add therefor --2723--;
Line 54, delete both occurrences of "395" and add therefor --2732--;
Line 54, delete both occurrences of "649" and add therefor --2986--;
Line 55, delete both occurrences of "686" and add therefor --3023--; and
Line 56, delete both occurrences of "1076" and add therefor --3413--.

<u>Column 60, Claim 9</u>
Line 49, delete both occurrences of "34" and add therefor --1125--.

Signed and Sealed this

Fourth Day of September, 2007

JON W. DUDAS
*Director of the United States Patent and Trademark Office*